United States Patent
Meggers et al.

(10) Patent No.: US 7,671,046 B2
(45) Date of Patent: Mar. 2, 2010

(54) METAL COMPLEX PROTEIN KINASE INHIBITORS

(75) Inventors: Eric Meggers, Philadelphia, PA (US); Lilu Zhang, Secane, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/178,145

(22) Filed: Jul. 23, 2008

(65) Prior Publication Data

US 2008/0275019 A1  Nov. 6, 2008

Related U.S. Application Data

(62) Division of application No. 11/045,331, filed on Jan. 31, 2005, now Pat. No. 7,488,817.

(60) Provisional application No. 60/540,591, filed on Feb. 2, 2004.

(51) Int. Cl.
*C07B 47/00* (2006.01)
*C07D 487/22* (2006.01)
*A01N 55/02* (2006.01)
*A61K 31/555* (2006.01)

(52) U.S. Cl. .......... 514/185; 540/145; 514/410

(58) Field of Classification Search ............ 540/145; 514/185, 410

See application file for complete search history.

(56) References Cited

U.S. PATENT DOCUMENTS

| | | |
|---|---|---|
| 6,451,838 B1 | 9/2002 | Moon et al. |
| 6,555,539 B2 | 4/2003 | Reich et al. |
| 6,593,357 B1 | 7/2003 | Green et al. |
| 6,613,776 B2 | 9/2003 | Knegtel et al. |

*Primary Examiner*—James O. Wilson
*Assistant Examiner*—Paul V. Ward
(74) *Attorney, Agent, or Firm*—Woodcock Washburn, LLP

(57) ABSTRACT

This inventive subject matter relates to novel metal complex protein kinases inhibitors, methods for making such compounds, and methods for using such compounds for treating diseases and disorders mediated by kinase activity.

13 Claims, 2 Drawing Sheets

METAL COMPLEX PROTEIN KINASE INHIBITORS

This application is a divisional of U.S. patent application Ser. No. 11/045,331 filed Jan. 31, 2005, which claims the benefit of U.S. Provisional Application No. 60/540,591 filed Feb. 2, 2004, the contents of which are hereby incorporated by reference in their entireties.

BACKGROUND OF THE INVENTIVE SUBJECT MATTER

1. Field of Inventive Subject Matter

The present inventive subject matter relates to novel metal complex protein kinases inhibitors, methods for making such compounds, and methods for using such compounds for treating diseases and disorders mediated by kinase activity.

2. Background

The development of small molecules that perturb specific protein functions is of great importance for probing biological processes and ultimately for the development of potent and safe drugs. Medicinal chemistry is predominately focused on the design of organic molecules, whereas the incorporation of inorganic components into drugs is much less investigated. Furthermore, in almost all metallopharmaceuticals, the metal ion possesses a reactive feature. We have found that certain organometallic and inorganic compounds are useful as structural scaffolds for enzyme inhibition. Such metal-ligand assemblies allow convergent synthetic approaches and give access to structural motifs that differ from purely organic molecules. Nature makes extended use of metals not only for their reactivity but also for structural purposes, as for example in zinc binding aspartate transcarbamoylase and zinc finger domains, or the calcium binding protein calmodulin.

Protein kinases regulate most aspects of cellular life and are one of the main drug targets. An example is the microbial alkaloid staurosporine, which is a very potent, but relatively nonspecific inhibitor of many protein kinases. Many staurosporine derivatives and related organic compounds with modulated specificities have been developed and several are in clinical trials as anticancer drugs. They all share an indolo[2,3-∀]carbazole aglycon which binds to the ATP binding site and can hydrogen bond with two conserved amino acids. For this class of inhibitors, specificity for a particular protein kinase can be achieved by the moiety which is attached to the indole nitrogen atoms.

Exemplary compounds and compositions in the patent database, which are claimed as protein kinase inhibitors, include the following:

U.S. Pat. No. 6,613,776, issued Sep. 2, 2003 to Knegtel, et al. discloses pyrazole compositions useful as protein kinase inhibitors, especially as inhibitors of aurora-2 and GSK-3, for treating diseases such as cancer, diabetes, and Alzheimer's disease.

U.S. Pat. No. 6,593,357, issued Jul. 15, 2003 to Green, et al. discloses pyrazole compositions useful as protein kinase inhibitors of ERK, for treating disease states in mammals that are alleviated by a protein kinase inhibitor, particularly diseases such as cancer, inflammatory disorders, restenosis, and cardiovascular disease.

U.S. Pat. No. 6,555,539, issued Apr. 29, 2003 to Reich, et al. discloses indazole compounds that modulate and/or inhibit cell proliferation, such as the activity of protein kinases, for mediating kinase-dependent diseases and treating cancer and other disease states associated with unwanted angiogenesis and/or cellular proliferation, such as diabetic retinopathy, neovascular glaucoma, rheumatoid arthritis, and psoriasis.

U.S. Pat. No. 6,451,838, issued Sep. 17, 2002 to Moon, et al. discloses 1-pyrrolidin-1-ylmethyl-3-(pyrrol-2-ylmethylidene)-2-indolinone derivatives for modulating the activity of protein kinases, methods of preparing same, along with pharmaceutical compositions comprising these compounds and methods of treating diseases related to abnormal protein kinase activity utilizing pharmaceutical compositions comprising these compounds.

Thus, there is a significant need in the art for more specific and effective protein kinase inhibitors, which can be targeted to specific tissues and/or disease states. Applicants have developed metal complexes that target the ATP binding site of protein kinases. Additional ligands in the coordination sphere of the metal ion undergo additional specific contacts with other parts of the active site, giving metal complex binders with high affinity and specificity for a particular protein kinase.

SUMMARY OF THE INVENTIVE SUBJECT MATTER

The present inventive subject matter relates to a compound of formula I

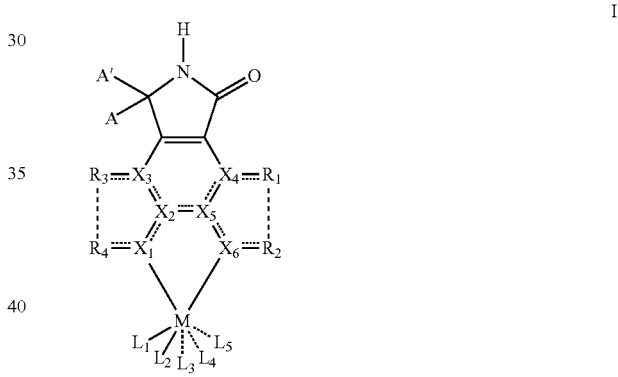

or a pharmaceutically acceptable salt, ester, or solvate thereof, wherein:

or a pharmaceutically acceptable salt, ester, or solvate thereof, wherein:

$X_1, X_2, X_3, X_4, X_5$, and $X_6$ are each independently selected from the group consisting of N, C, S, O, B, and Si;

$R_1, R_2, R_3$, and $R_4$ are each independently selected from the group consisting of:

1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, $C_1$-$C_9$ alkoxy, $C_2$-$C_9$ alkenyloxy, $C_3$-$C_8$ cycloalkyl, $C_5$-$C_7$ cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, straight or branched chain $C_1$-$C_9$ alkyl, straight or branched chain $C_1$-$C_9$ alkyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O—($C_1$-$C_9$ straight or branched chain alkyl), straight or branched chain $C_2$-$C_9$ alkenyl or alkynyl, and straight or branched chain $C_2$-$C_9$ alkenyl or alkynyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O—($C_2$-$C_9$ straight or branched chain alkenyl), and Ar, and/or $R_1$ and $R_2$ are taken together to form a mono-, bi- or tricyclic, carbo- or heterocyclic ring, wherein the ring is either unsubstituted or substituted, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S, and/or $R_3$ and $R_4$ are taken together to form a mono-, bi- or tricyclic, carbo- or heterocyclic ring, wherein the ring is either unsubstituted or substituted, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

Ar is a mono-, bi- or tricyclic, carbo- or heterocyclic ring, wherein the ring is either unsubstituted or substituted in one or more position(s) with halo, hydroxyl, nitro, trifluoromethyl, $C_1$-$C_6$ straight or branched chain alkyl or alkenyl, $C_1$-$C_4$ alkoxy, $C_1$-$C_4$ alkenyloxy, phenoxy, benzyloxy, or amino; wherein the individual ring size for a monocyclic ring is 5-7 members and for a bicyclic or tricyclic ring is 3-8 members; and wherein the heterocyclic ring contains 1-5 heteroatom(s) selected from the group consisting of O, N, and S;

M is selected from the group consisting of Ru, Pt, Tc, Re, Os, Rh, Ir, Pd, Au, Cu, and any other metal or half-metal;

A and A' are each independently selected from the group consisting of hydrogen, hydroxy, hydroxymethyl, $C_1$-$C_6$ straight or branched chain alkyl, $C_2$-$C_6$ straight or branched chain alkenyl, O—($C_1$-$C_6$ straight or branched chain alkyl), and O—($C_2$-$C_6$ straight or branched chain alkenyl), or A and A' are taken together as =O; and each $L_1$-$L_n$ is independently selected from the group consisting of a monodentate ligand capable of acting as a ligand for said metal M, and/or $L_1$ and $L_2$ are taken together as a bidentate ligand capable of acting as a ligand for said metal M, and/or $L_1$, $L_2$, and $L_3$ are taken together as a tridentate ligand capable of acting as a ligand for said metal M, and/or $L_1$, $L_2$, $L_3$, and $L_4$ are taken together as a tetradentate ligand capable of acting as a ligand for said metal M; and n is 2, 3, 4, or 5.

The present inventive subject matter also relates to a pharmaceutical composition comprising:

(i) a therapeutically effective amount of the compound of formula II

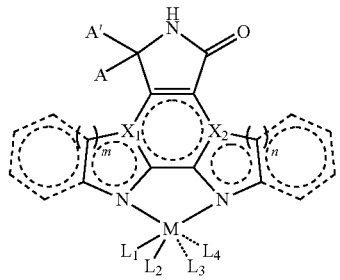

or a pharmaceutically acceptable salt, ester, or solvate thereof, wherein:

A is H,

A' is H, or

A and A' taken together are =O;

$X_1$ is N or C;

$X_2$ is N or C;

m is 1 or 2;

n is 1 or 2;

M is Ru or Pt;

each $L_1$, $L_2$, $L_3$, and $L_4$ is independently selected from the group consisting of monodentate ligands capable of acting as a ligand for said metal M, and/or $L_1$ and $L_2$ are taken together as a bidentate ligand capable of acting as a ligand for said metal M, and/or $L_3$ and $L_4$ are taken together as a bidentate ligand capable of acting as a ligand for said metal M; and (ii) a pharmaceutically acceptable carrier.

The present inventive subject matter further relates to a method for treating cancer in an animal in need thereof, which comprises administering to said animal an effective amount of a compound of formula II

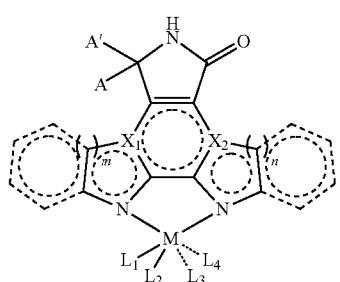

or a pharmaceutically acceptable salt, ester, or solvate thereof, wherein:

A is H,

A' is H, or

A and A' taken together are =O;

$X_1$ is N or C;

$X_2$ is N or C;

m is 1 or 2;

n is 1 or 2;

M is Ru or Pt; and each $L_1$, $L_2$, $L_3$, and $L_4$ is independently selected from the group consisting of monodentate ligands capable of acting as a ligand for said metal M, and/or $L_1$ and $L_2$ are taken together as a bidentate ligand capable of acting as a ligand for said metal M, and/or $L_3$ and $L_4$ are taken together as a bidentate ligand capable of acting as a ligand for said metal M, wherein one or more of said $L_1$, $L_2$, $L_3$, and $L_4$ additionally comprises a moiety for producing cell cycle arrest or apoptosis in a target cancer cell.

Further, the present inventive subject matter relates to a compound of formula III

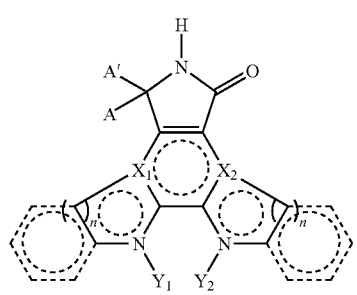

III or a pharmaceutically acceptable salt, ester, or solvate thereof, wherein:

A is H,
A' is H, or
A and A' taken together are =O;
$X_1$ is N or C;
$X_2$ is N or C;
$Y_1$ is selected from the group consisting of H, $CH_3$, BOC, and nothing;
$Y_2$ is selected from the group consisting of H, $CH_3$, BOC, and nothing;
m is 1 or 2; and
n is 1 or 2.

BRIEF DESCRIPTION OF THE DRAWINGS

FIG. 2 is a drawing which depicts the X-ray structure of compound 12a.

DETAILED DESCRIPTION OF THE INVENTIVE SUBJECT MATTER

Definitions

Figure 1:
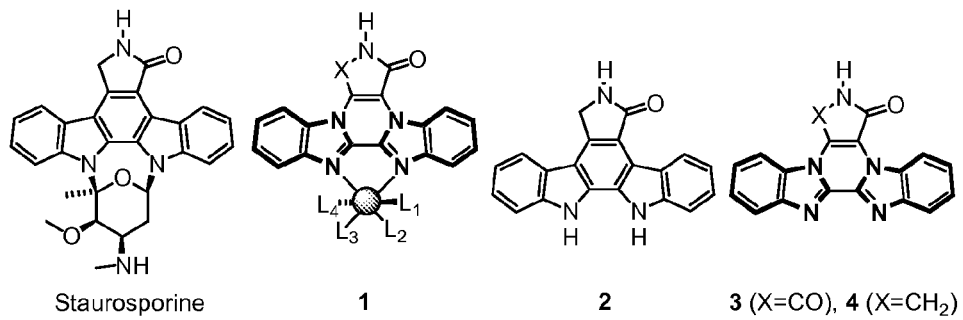
FIG. 1 is a drawing which depicts inventive and prior art compounds.

The term "therapeutically effective amount" as used herein refers to that amount of a compound which will contribute to the cancer-treating ability of the composition.

The term "treating" as used herein refers to partial or total inhibition of a disease state, disease progression, or disorder.

The term "preventing" as used herein refers to either preventing the onset of clinically evident disease or disorder altogether, or preventing the onset of a preclinically evident stage of a disease or disorder in individuals at risk.

The term "enhancing" the biological activity, function, health, or condition of an organism refers to the process of augmenting, fortifying, strengthening, or improving.

The term "isomers" refer to different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

The term "pharmaceutically acceptable salt, ester, or solvate" refers to a salt, ester, or solvate of a subject compound which possesses the desired pharmacological activity and which is neither biologically nor otherwise undesirable. A salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Also, the basic nitrogen-containing groups can be quarternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides, such as benzyl and phenethyl bromides; and others. Water or oil-soluble or dispersible products are thereby obtained.

The term "ligand" as used herein refers to any group which can form a coordination complex with a metal. A ligand offering one group for attachment to the metal is termed monodentate; two groups, bidentate; three or more groups, polydentate. A ligand may attach to the metal atom by covalent or ionic bond(s). Many compounds, too numerous to fully enumerate here, can act as ligands; common ligands include, but are not limited to, derivatives of amines (e.g. ethylenediamine), aldehydes and ketones, carboxylic acids (e.g. ethylenediaminetetraacetic acid (EDTA)), sulfonyl- and mercapto-derivative groups, phosphoryls and other phosphorus derivatives, hydroxamic acid derivatives, and various combinations thereof. Other examples of useful metal ligands include, without limitation, mercapto derivatives, hydroxamic acid derivatives, phosphorus derivatives (particularly those of the general formula X—P(O)(OH)—R, wherein R is as defined above for $R_1$), carboxyl derivatives, N-carboxyalkyl derivatives, aldehydes, ketones, and combinations thereof. In particular, useful ligands include, without limitation, derivatives of dicarboxylic acids, ∃-diketones, ∀-hydroxycarboxylic acids, alkyl and aryl diamines, ∀- and ∃-aminocarboxylates (including amino acid derivatives), thioethers, xanthates, dithiocarbamates, dithiocarboxylates, thioglycolates, thiols, and diphosphines.

The term "monodentate ligand" as used herein refers to an atom or compound which has one lone pair of electrons by which it can attach to another atom or compound. For example, many simple anions, or Lewis bases, can act as monodentate ligands, including, without limitation, chloride ion, hydroxide ion, water, and ammonia. In addition, a monodentate ligand can also be a compound which coordinates through a pi-bond, such as an alkene.

The term "bidentate ligand" as used herein refers to an atom or compound which has two lone pairs of electrons by which it can attach to another atom or compound. Similarly, the terms "tridentate ligand" and "tetradentate ligand" as used herein refer to an atom or compound which has, respectively, three and four lone pairs of electrons by which it can attach to another atom or compound.

The Inventive Compounds

The present inventive subject matter relates to the compounds of formulas I, II, and III.

The development of small molecules that perturb specific protein functions is of great importance for probing biological processes and ultimately for the development of potent and safe drugs. Medicinal chemistry is predominately focused on the design of organic molecules, whereas the incorporation of inorganic components into drugs is much less investigated. Furthermore, in almost all metallopharmaceuticals, the metal ion possesses a reactive feature. We have found that certain organometallic and inorganic compounds are useful as structural scaffolds for enzyme inhibition. Such metal-ligand assemblies allow convergent synthetic approaches and give access to structural motifs that differ from purely organic molecules.

Protein kinases regulate most aspects of cellular life and are one of the main drug targets. The microbial alkaloid staurosporine is a very potent, but relatively nonspecific inhibitor of many protein kinases. Many staurosporine derivatives and related organic compounds with modulated specificities have been developed and several are in clinical trials as anticancer drugs. They all share an indolo[2,3-∀] carbazole aglycon (1) which binds to the ATP binding site and can hydrogen bond with two conserved amino acids. For this class of inhibitors, specificity for a particular protein kinase can be achieved by the moiety which is attached to the indole nitrogen atoms.

As depicted in FIG. 1, we have determined that by replacing the indolocarbazole alkaloid scaffold with metal complex (2), elaborate structures could be assembled in an efficient manner by variation of ligand(s) (Lx). Key components of our design are ligands (3) and (4), derived from the indolocarbazole aglycon (1) by just replacing two carbon against two nitrogen atoms. This transformation does not change the shape of the ligand but generates two benzimidazole moieties that can function as coordination sites for the metal center. The remaining coordination sites at the metal center can become filled-up by ligands $L_1$ to $L_4$ and substitute for the carbohydrate moiety, with the metal center serving as a "glue" for holding all parts together.

Medicinal Chemistry of Small Organic Compounds. New technologies for drug discovery such as combinatorial chemistry, high-throughput screening, computer assisted drug design, and virtual compound screening in silico emerged during the last 20 years. Interestingly, despite these clearly extremely powerful techniques, the development of high affinity and specific compounds for a given target is still a great and often unsolved challenge. For example, not a single existing kinase inhibitor is specific for a particular kinase. It is also surprising that despite all technical advances the number of new drug launches by the top 20 pharmaceutical companies is not increasing despite an increase in spending into research and development.

One limiting factor can be found in the synthesis itself of the drug candidates. For example, complex natural products often show promising biological activities and would be interesting lead structures, but they often require too many reaction steps including time consuming purifications and are therefore often not practical as drug scaffolds. For example, bryostatin, a member of marine derived macrolactones, is extremely potent against numerous cancers but its synthesis includes more than 60 reaction steps. The Wender group has addressed this issue by developing analogs with improved synthetic accessibility, but the synthesis is still around 20 steps long. There is clearly a need for simplification of synthetic approaches. Additionally, the desire to make large compound libraries has led to the use of reliable chemistry and simple scaffolds. It is therefore no surprise that the diversity of topological shapes of known drugs is extremely low. A report about the analysis of the Comprehensive Medicinal Chemistry (CMC) database revealed that half of the known drugs fall into only 32 shape categories (out of more than 5000 compounds analyzed). Most of the 32 frameworks contain at least two six-membered rings linked or fused together.

It can be concluded that the popularity of molecular scaffolds for drugs is dictated by synthetic availability and the adaptability to combinatorial chemistry.

Metallopharmaceuticals. Metal ions and metal complexes are important in diagnosis and therapy and metal ions from allover the periodic table of elements are being used. In all metallopharmaceuticals, the metal-ion bears the key feature of the mechanism. For example, the highly efficient anticancer drug cisplatin reacts with DNA by crosslinking guanine bases which eventually leads to apoptosis.

One of the rare reported metal complexes in which the metal plays only a structural role is the copper complex diaqua[bis (2-pyridylcarbonyl)amido]copper(II) nitrate dihydrate. This complex was found to fit in the enzyme active site by modeling and experimentally characterized to be a competitive inhibitor of HIV-1 protease. To the best of the authors knowledge, not a single FDA approved metallopharmaceutical exists in which the metal plays a purely structural role in organizing the attached organic ligands.

Metal Complexes as Structural Templates. Metal coordination has been proven to be a powerful tool for the creation of artificial receptors, for the self-assembly of elaborated nanostructures, for the assembly of biomimetic structures such as DNA mimicking helicates, for the synthesis of dendrimers, and the generation of liquid crystals. In addition to playing an important role in the assembly process, the metal complex often fulfills an important structural role in organizing the surrounding organic part. Ligand exchange kinetics can be tuned by the nature of the metal and its oxidation state and a change in coordination number and geometry allows a modification of organization of the attached organic ligands. Thus, metal complexes should clearly be very interesting structural templates for the creating of enzyme inhibitors. The metal center will allow efficient assembly reactions and will give the opportunity to generate structural motifs that are not easily accessible with purely organic compounds.

Metal Toxicity. A significant concern in using metal containing drugs is the potential toxicity of the metal. Clearly many essential and non-essential metals or metal compounds of Be, Cr, Cd, Ni, Co, Pb, and Hg are toxic and/or carcinogenic. However, it is important to recognize that the action of these metals is closely associated to their oxidation state and involvement of all additional metal ligands. For example, chromium is cancerogenic in the form of $CrO_4^{2-}$, but not in the oxidation state +2 and +3, because only the chromate ion can enter the cells through a specific anion transporter. In another example, cisplatin, $PtCl_2(NH_3)_2$, is one of the most successful anticancer drugs and also very toxic. The toxicity is related to the reactivity of the metal center due to exchange of the chlorides and therefore its potency and toxicity are highly dependent on the substituents. A reduction in reactivity correlates with a reduction of toxicity. From this it can be concluded that toxicity and function of metals are closely connected to the nature of the ligands. A metal complex that has an inert coordination sphere might not display any "metal-specific" toxicity itself.

In a metal-containing compound, the ligand is often an organic compound that binds the metal ion and modifies the physical and chemical properties of the ion. Thus, kinetic stability of the metal-ligand assembly will be an important factor for toxicity. Almost nothing is known about short and long term toxicity and pharmacokinetics of kinetically inert metal complexes and the risk of metal accumulation.

Stability of Metal Complexes. The rate of ligand substitutions is an important parameter for the stability of metal complexes in biological environment. It depends on the nature of the ligand and importantly on the metal itself and its oxidation state. Metals of the first d-series such as $Mn^{2+}$, $Fe^{2+/3+}$, $Co^{2+}$, $Ni^{2+}$, $Cu^{2+}$, and $Zn^{2+}$ generally undergo rapid equilibration. Exceptions in the first row are classical coordination complexes of $Cr^{3+}$ and $Co^{3+}$ because of their ability to from strong-field $d^3$ and $d^6$ complexes, respectively, and some organometallic scaffolds such as ferrocene and chromium plus iron carbonyl compounds. Among the second and third d-series complexes the inertness is generally much higher, which reflects the high ligand field stabilization energy and the strength of the metal-ligand bonds. For example, Ru—N and Pt—N bonds can be considered as completely inert against substitution at ambient temperature and can thus de facto be treated like covalent bonds. Additionally, the ability to tune the kinetic stability of coordinative bonds without changing the overall structure, can be a useful advantages in the drug discovery process.

Our initial compounds showed a limited stability of the ruthenium complexes (only one complex was completely stable), probably due to the unfavorable biting angle of the bisbenzimidazole ligand. We have also synthesized a more stable second-generation ligand S5, which solves the stability problem and even yields more potent inhibitors. The synthesis is shown in Scheme 2.

Metal Complexes as Protein Kinase Inhibitors. Protein kinases regulate most aspects of cellular function in eukaryotes, including metabolism, transcription, cell cycle progression, apoptosis, differentiation, and intercellular communication. Mutations and dysregulation of protein kinases play causal roles in many human diseases, making kinases an important therapeutic target. Protein kinases are among the largest enzyme families with more than 500 putative protein kinase genes, which makes it challenging to find specific inhibitors. An in vitro study of the specificity of 28 commercially available protein kinase inhibitors, some with supposedly high specificity, revealed that all but two drugs had more than one protein target. Clearly, novel and if possible general strategies have to be sought in order to solve the important problem of developing specific inhibitors for enzymes that are members of large and homologous enzyme families.

Typically, protein kinase inhibitors bind to the ATP binding site by mimicking the hydrogen-bonding pattern of the adenine base. Given the high degree of amino acid conversation within the ATP binding pocket of protein kinases, the design of highly selective ATP-competitive inhibitors was long believed to be impossible. This notion has be changed and successful examples have demonstrated that it is possible to take advantage of the small differences between the structures of the APT binding sites, even between closely related protein kinases. Inhibitors are generally made up of a heterocyclic core that roughly mimics adenine. Like adenine, these templates form hydrogen bonds with the extended coil stretch of the kinase. Affinity and selectivity for a particular kinase are achieved by modifying one of the main templates resulting in modulated interactions with the ATP binding site.

Formula I

A compound of formula I refers to:

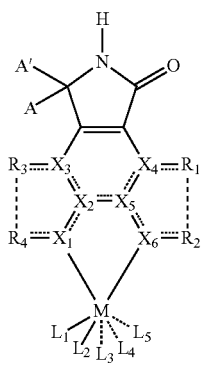

or a pharmaceutically acceptable salt, ester, or solvate thereof, wherein:

$X_1, X_2, X_3, X_4, X_5$, and $X_6$ are each independently selected from the group consisting of N, C, S, O, B, and Si;

$R_1, R_2, R_3$, and $R_4$ are each independently selected from the group consisting of:

1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, $C_1$-$C_9$ alkoxy, $C_2$-$C_9$ alkenyloxy, $C_3$-$C_8$ cycloalkyl, $C_5$-$C_7$ cycloalkenyl, carbonyl, carboxy, carboxylic and heterocyclic moieties cyano, diazo, ester, formanilido, halo, haloalkyl, hydrogen, hydroxy, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, straight or branched chain $C_1$-$C_9$ alkyl, straight or branched chain $C_1$-$C_9$ alkyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O—($C_1$-$C_9$ straight or branched chain alkyl), straight or branched chain $C_2$-$C_9$ alkenyl or alkynyl, and straight or branched chain $C_2$-$C_9$ alkenyl or alkynyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O—($C_2$-$C_9$ straight or branched chain alkenyl), and Ar, and/or $R_1$ and $R_2$ are taken together to form a mono-, bi- or tricyclic, carbo- or heterocyclic ring, wherein the ring is either unsubstituted or substituted, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S, and/or $R_3$ and $R_4$ are taken together to form a mono-, bi- or tricyclic, carbo- or heterocyclic ring, wherein the ring is either unsubstituted or substituted, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S;

Ar is a mono-, bi- or tricyclic, carbo- or heterocyclic ring, wherein the ring is either unsubstituted or substituted in one or more position(s) with halo, hydroxyl, nitro, trifluoromethyl, $C_1$-$C_6$ straight or branched chain alkyl or alkenyl, $C_1$-$C_4$ alkoxy, $C_1$-$C_4$ alkenyloxy, phenoxy, benzyloxy, or amino; wherein the individual ring size for a monocyclic ring is 5-7 members and for a bicyclic or tricyclic ring is 3-8 members; and wherein the heterocyclic ring contains 1-5 heteroatom(s) selected from the group consisting of O, N, and S;

M is selected from the group consisting of Ru, Pt, Tc, Re, Os, Rh, Ir, Pd, Au, Cu, and any other metal or half-metal;

A and A' are each independently selected from the group consisting of hydrogen, hydroxy, hydroxymethyl, $C_1$-$C_6$ straight or branched chain alkyl, $C_2$-$C_6$ straight or branched chain alkenyl, O—($C_1$-$C_6$ straight or branched chain alkyl), and O—($C_2$-$C_6$ straight or branched chain alkenyl), or A and A' are taken together as =O; and each $L_1$-$L_n$ is independently selected from the group consisting of a monodentate ligand capable of acting as a ligand for said metal M, and/or $L_1$ and $L_2$ are taken together as a bidentate ligand capable of acting as a ligand for said metal M, and/or $L_1$, $L_2$, and $L_3$, when all are present, are taken together as a tridentate ligand capable of acting as a ligand for said metal M, and/or $L_1$, $L_2$, $L_3$, and $L_4$, when all are present, are taken together as a tetradentate ligand capable of acting as a ligand for said metal M; and n is 2, 3, 4, or 5.

In an alternate aspect of the inventive subject matter, each said $L_1$-$L_n$, individually as a monodentate ligand or taken together as a bidentate ligand, a tridentate ligand, or a tetradentate ligand, is selected from the group consisting of halo, hydroxy, carbonyl, amine, nitro, sulfhydryl, pyridine, thiolate, histidine, methionine, cysteine, dimethylsulfoxide, substituted or unsubstituted pyridines, substituted or unsubstituted amines, substituted or unsubstituted diamines, substituted or unsubstituted thiols, substituted or unsubstituted dithiols, substituted or unsubstituted imidazoles, substituted or unsubstituted pyrazoles, substituted or unsubstituted benzimidazoles, substituted or unsubstituted 1,4-dienes, substituted or unsubstituted 2-(aminomethyl)pyridines, substituted or unsubstituted 2-iminopyridines, substituted bipyridines, substituted or unsubstituted phenanthrolines, substituted or unsubstituted 8-hydroxyquinolines, substituted or unsubstituted 6-mercaptopurines, and substituted or unsubstituted phosphines.

In a further aspect of the inventive subject matter, said $X_1$, $X_2$, $X_3$, $X_4$, $X_5$, and $X_6$ are each independently selected from the group consisting of N and C.

In another aspect of the inventive subject matter, said M is Ru or Pt.

In another aspect of the inventive subject matter, said $R_1$ and $R_2$ are taken together to form a monocyclic 5 or 6 membered ring, or a bicyclic indene, indene derivative, naphthalene, or naphthalene derivative ring, and wherein said ring is carbocyclic or heterocyclic.

In a preferred embodiment, said indene or naphthalene derivative refers to a fully unsaturated, partially unsaturated, or fully saturated ring structure having the same number of ring atoms as the base indene or naphthalene ring. By way of non-limiting example, an indene derivative includes indole, benzimidazole, indazole, and the like.

In yet another aspect of the inventive subject matter, said $R_3$ and $R_4$ are taken together to form a monocyclic 5 or 6 membered ring, or a bicyclic indene, indene derivative, naphthalene, or naphthalene derivative ring, and wherein said ring is carbocyclic or heterocyclic.

Formula II

A compound of formula II refers to:

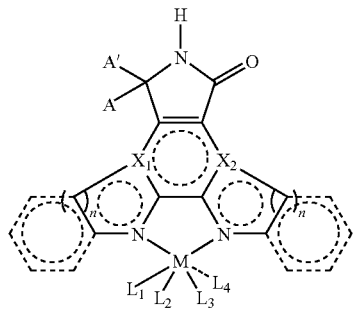

II or a pharmaceutically acceptable salt, ester, or solvate thereof, wherein:

A is H,

A' is H, or

A and A' taken together are =O;

$X_1$ is N or C;

$X_2$ is N or C;

m is 1 or 2;

n is 1 or 2;

M is Ru or Pt; and each $L_1$, $L_2$, $L_3$, and $L_4$ is independently selected from the group consisting of monodentate ligands capable of acting as a ligand for said metal M, and/or $L_1$ and $L_2$ are taken together as a bidentate ligand capable of acting as a ligand for said metal M, and/or $L_3$ and $L_4$ are taken together as a bidentate ligand capable of acting as a ligand for said metal M.

In another aspect of the inventive subject matter, at least one of $X_1$ and $X_2$ is N.

In a preferred embodiment, $X_1$ and $X_2$ are each N.

In yet another aspect of the inventive subject matter, m is 1 and n is 1.

In a further aspect of the inventive subject matter, said monodentate ligand is selected from the group consisting of halo, hydroxy, carbonyl, amine, nitro, sulfhydryl, pyridine, thiolate, histidine, methionine, cysteine, and dimethylsulfoxide.

In an alternate aspect of the inventive subject matter, said bidentate ligand is selected from the group consisting of substituted or unsubstituted pyridines, amines, diamines, thiols, dithiols, imidazoles, pyrazoles, benzimidazoles, 1,4-dienes, 2-(aminomethyl)pyridines, 2-iminopyridines, substituted bipyridines, phenanthrolines, 8-hydroxyquinolines, and 6-mercaptopurines.

In yet another aspect of the inventive subject matter, said compound is selected from the group consisting of:

In yet another aspect of the inventive subject matter, said compound is selected from the group consisting of:

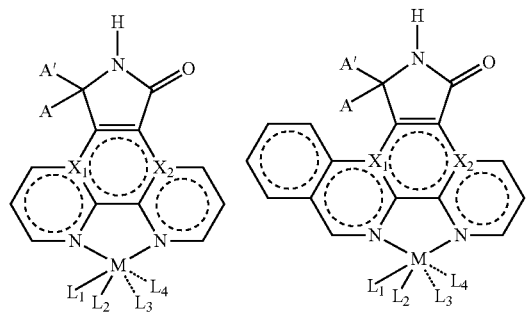

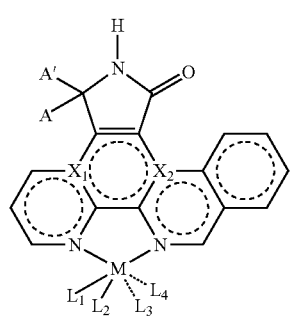

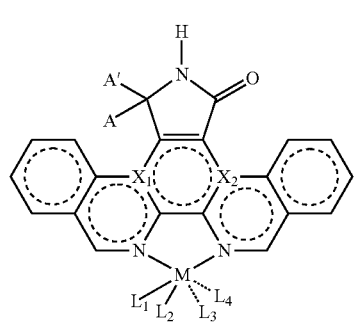

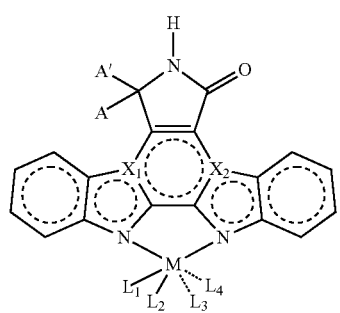

-continued

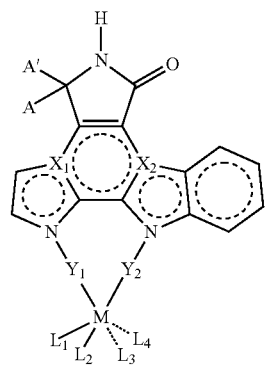

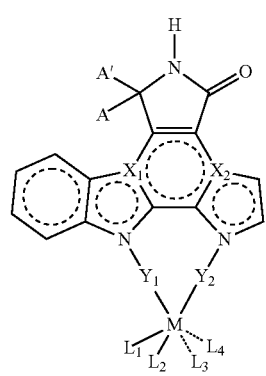

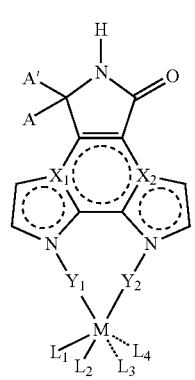 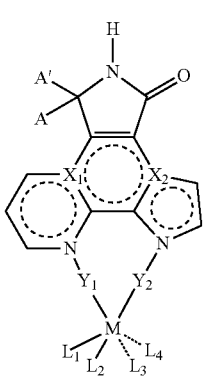

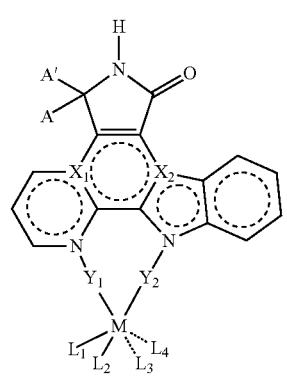

-continued

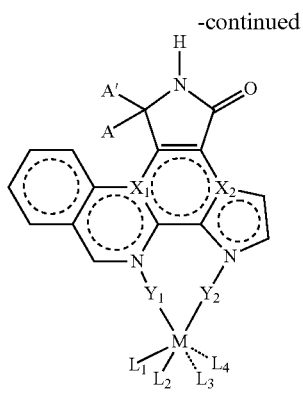

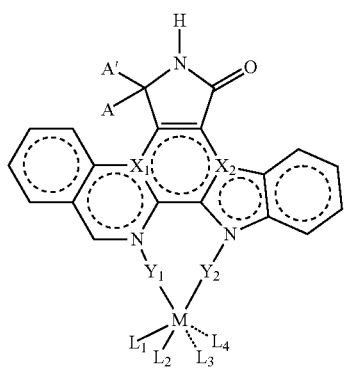

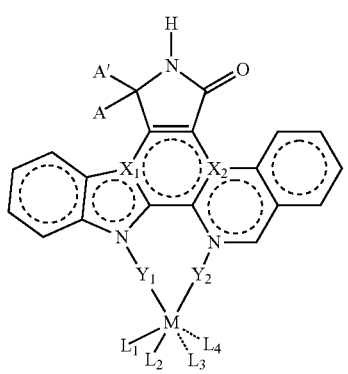

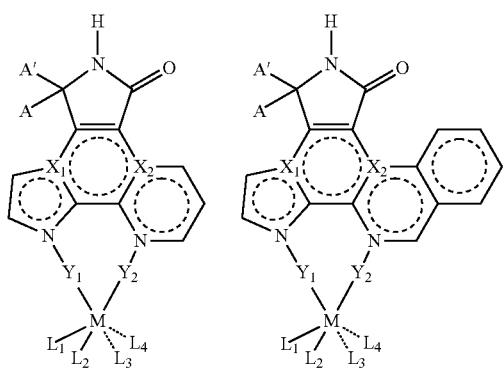

-continued

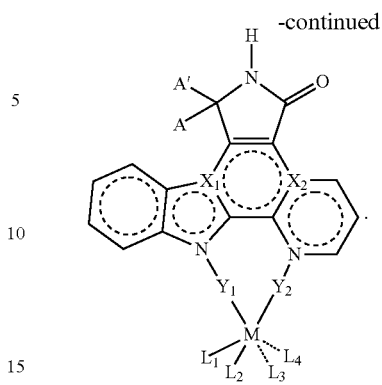

The synthesis of ruthenium complexes with unprotected maleimide nitrogens was accomplished by using the TBDMS-modified ligand 8. Accordingly, reaction of 8 with cis-RuCl$_2$(DMSO)$_4$ yielded diastereoselectively the unprotected ruthenium complex 12b in one step. Reaction of 8 with Ru(COD)(CH$_3$CN)$_2$Cl$_2$ followed by treatment with TBAF yielded 13. Refluxing the lactam 4 in ethanol with Ru(bpy)$_2$(EtOH)$_2^{2+}$, generated from Ru(bpy)$_2$Cl$_2$ and AgOSO$_2$CF$_3$ in situ, yielded the ionic complex 14.

All three metal complex scaffolds are air stable and can be stored on the bench over weeks without any signs of decomposition. Bipyridine complex 14 is completely stable in a 1:1 water/DMSO solution for 12 hours and even can withstand a 1 mM methanolic solution of 2-mercaptoethanol for 3 hours without any decomposition. Time-dependent 1H-NMR measurements show that the compounds 12b and 13 slowly release ligand 3 in 1:1 water/DMSO mixtures, with half-lives of 8 and 3 hours, respectively. However, their stability was sufficient for examining their potential as protein kinase inhibitors.

Formula III

A compound of formula III refers to:

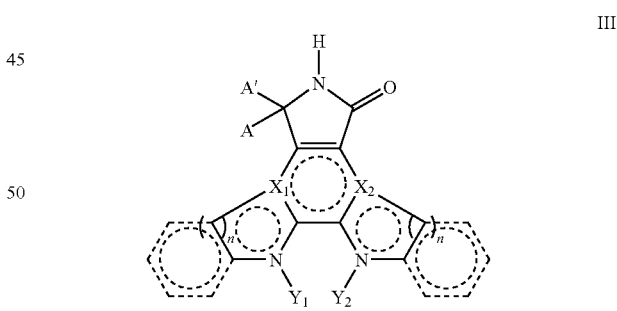

III or a pharmaceutically acceptable salt, ester, or solvate thereof, wherein:
A is H,
A' is H, or
A and A' taken together are =O;
X$_1$ is N or C;
X$_2$ is N or C;
Y$_1$ is selected from the group consisting of H, CH$_3$, BOC, and nothing;
Y$_2$ is selected from the group consisting of H, CH$_3$, BOC, and nothing;

m is 1 or 2; and
n is 1 or 2.
In a further aspect of the inventive subject matter, at least one of $X_1$ and $X_2$ is N.
In a preferred embodiment, $X_1$ and $X_2$ are each N.
In another aspect of the inventive subject matter, m is 1 and n is 1.
In a preferred embodiment, said compound is selected from the group consisting of:
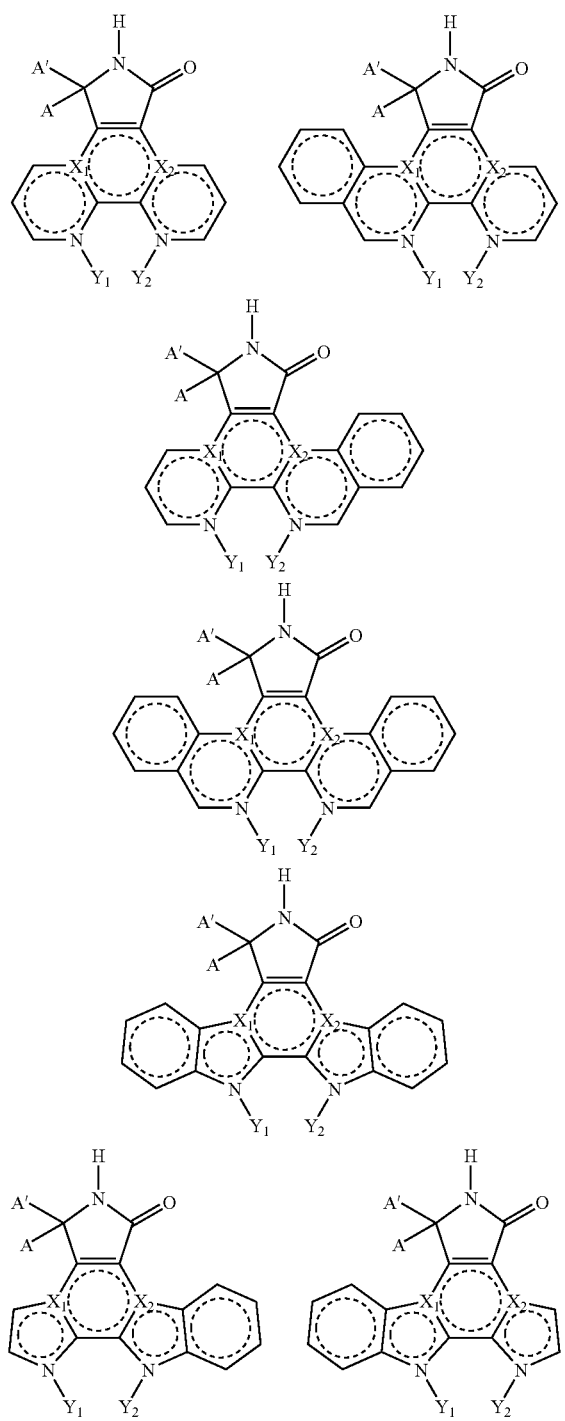
-continued
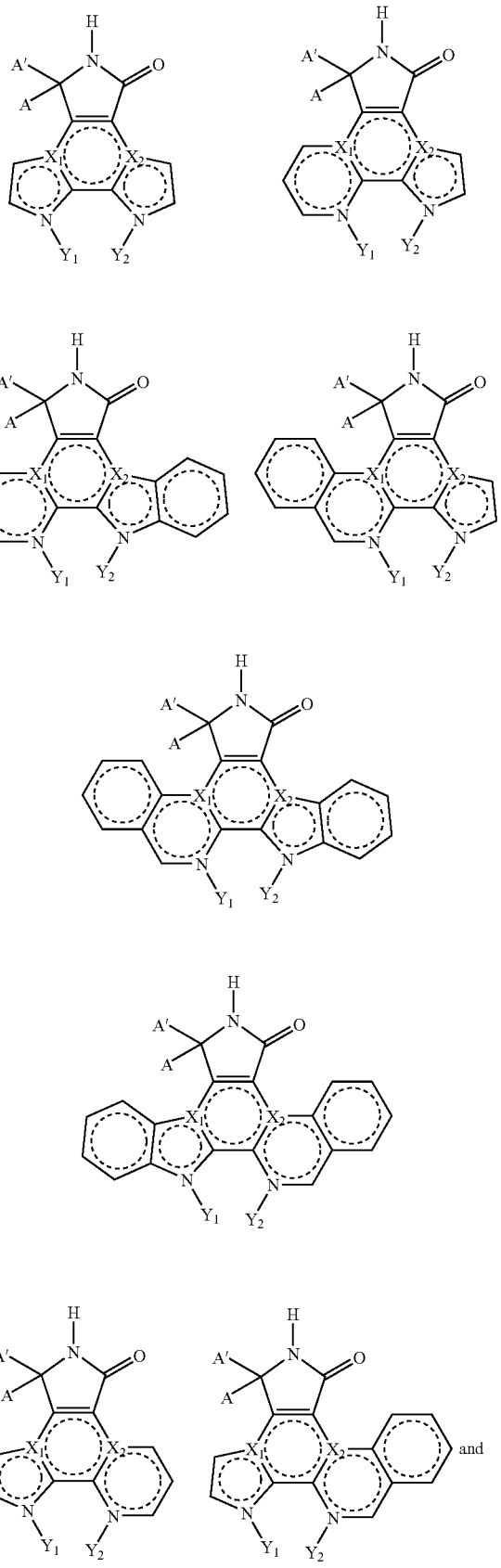

-continued

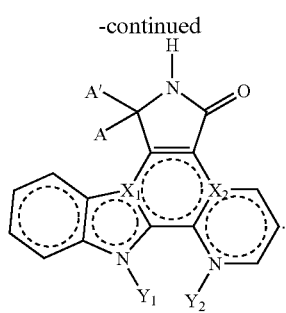

Pharmaceutical Compositions

The present inventive subject matter also relates to a pharmaceutical composition comprising:

(i) a therapeutically effective amount of the formula II

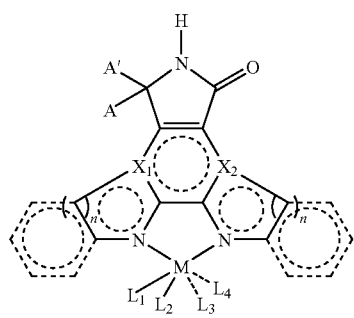

II or a pharmaceutically acceptable salt, ester, or solvate thereof, wherein:

A is H,
A' is H, or
A and A' taken together are =O;
$X_1$ is N or C;
$X_2$ is N or C;
m is 1 or 2;
n is 1 or 2;
M is Ru or Pt;
each $L_1$, $L_2$, $L_3$, and $L_4$ is independently selected from the group consisting of monodentate ligands capable of acting as a ligand for said metal M, and/or
$L_1$ and $L_2$ are taken together as a bidentate ligand capable of acting as a ligand for said metal M, and/or
$L_3$ and $L_4$ are taken together as a bidentate ligand capable of acting as a ligand for said metal M; and (ii) a pharmaceutically acceptable carrier.

In another aspect of the inventive subject matter, at least one of $X_1$ and $X_2$ is N.

In a preferred embodiment, $X_1$ and $X_2$ are each N.

In yet another aspect of the inventive subject matter, m is 1 and n is 1.

In a further aspect of the inventive subject matter, said monodentate ligand is selected from the group consisting of halo, hydroxy, carbonyl, amine, nitro, sulfhydryl, pyridine, thiolate, histidine, methionine, cysteine, and dimethylsulfoxide.

In an alternate aspect of the inventive subject matter, said bidentate ligand is selected from the group consisting of substituted or unsubstituted pyridines, amines, diamines, thiols, dithiols, imidazoles, pyrazoles, benzimidazoles, 1,4-dienes, 2-(aminomethyl)pyridines, 2-iminopyridines, substituted bipyridines, phenanthrolines, 8-hydroxyquinolines, and 6-mercaptopurines.

In yet another aspect of the inventive subject matter, said compound is selected from the group consisting of:

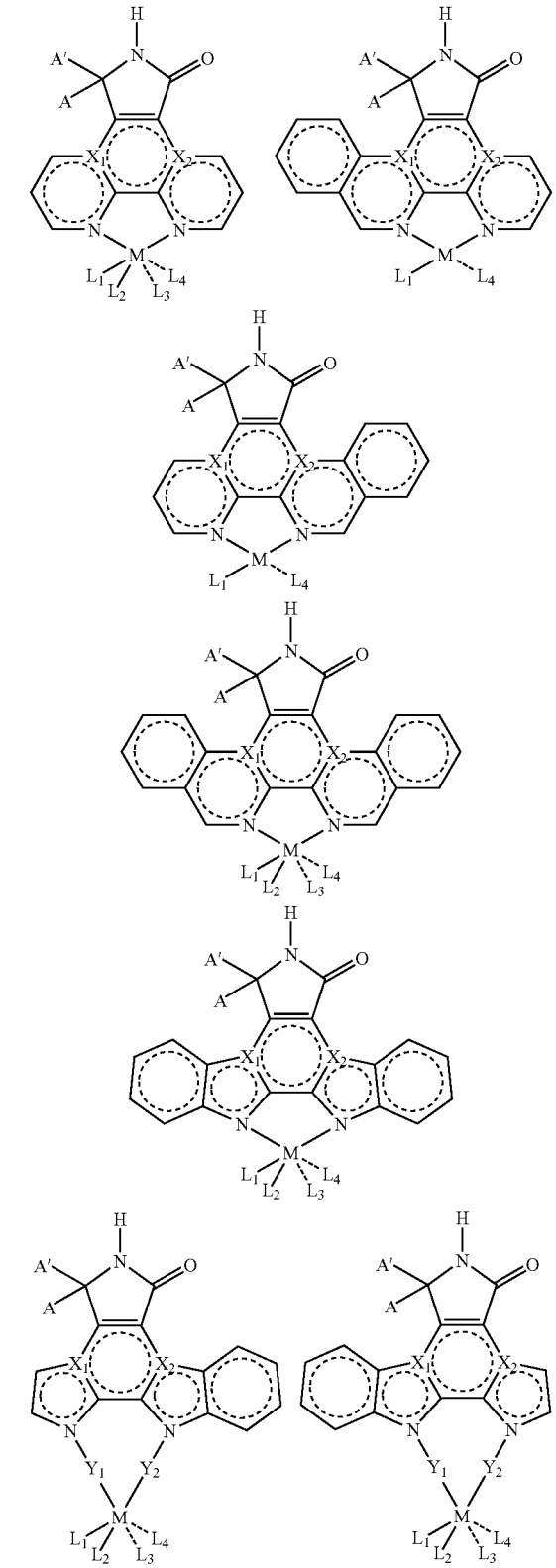

-continued

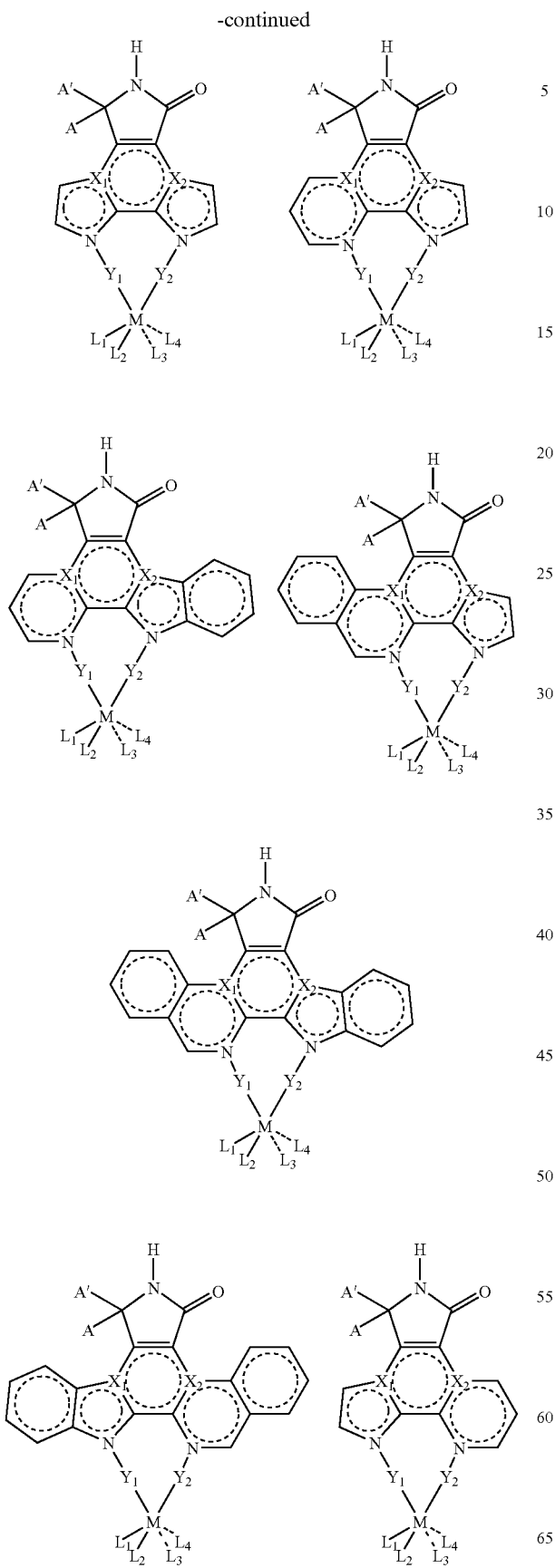

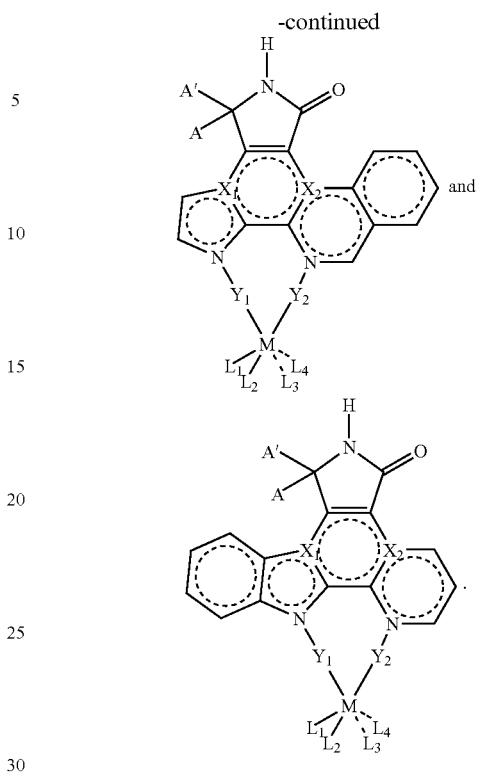

The novel pharmaceutical compositions of the inventive subject matter include a therapeutically effective amount of the active agent indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the present inventive subject matter.

The compounds of the inventive subject matter are preferably delivered to the patient by means of a pharmaceutically acceptable carrier. Such carriers are well known in the art and generally will be in either solid or liquid form. Solid form pharmaceutical preparations which may be prepared according to the present inventive subject matter include powders, tablets, dispersible granules, capsules, cachets and suppositories. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water/propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents. Liquid pharmaceutical preparations may comprise up to 100% by weight of the subject active agent.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the inventive subject matter may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the present inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857-884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

It is not expected that compounds of the present inventive subject matter will display significant adverse interactions with other synthetic or naturally occurring substances. Thus, a compound of the present inventive subject matter may be administered in combination with other compounds and compositions useful for . . . . In particular the compounds of the present inventive subject matter may be administered in combination with other compounds of the present inventive subject matter; other anticancer substances; etc.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the present therapeutic agents of the inventive subject matter.

Methods of the Present Inventive Subject Matter

The present inventive subject matter relates to a method for treating cancer in an animal in need thereof, which comprises administering to said animal an effective amount of a compound of formula II

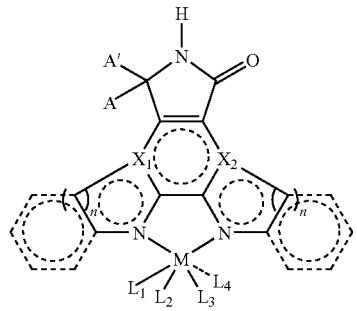

or a pharmaceutically acceptable salt, ester, or solvate thereof, wherein:
A is H,
A' is H, or
A and A' taken together are =O;
$X_1$ is N or C;
$X_2$ is N or C;
m is 1 or 2;
n is 1 or 2;
M is Ru or Pt; and
each $L_1$, $L_2$, $L_3$, and $L_4$ is independently selected from the group consisting of monodentate ligands capable of acting as a ligand for said metal M, and/or
$L_1$ and $L_2$ are taken together as a bidentate ligand capable of acting as a ligand for said metal M, and/or
$L_3$ and $L_4$ are taken together as a bidentate ligand capable of acting as a ligand for said metal M,
wherein one or more of said $L_1$, $L_2$, $L_3$, and $L_4$ additionally comprises a moiety for producing cell cycle arrest or apoptosis in a target cancer cell.

In another aspect of the inventive subject matter, at least one of $X_1$ and $X_2$ is N.

In a preferred embodiment, $X_1$ and $X_2$ are each N.

In yet another aspect of the inventive subject matter, m is 1 and n is 1.

In a further aspect of the inventive subject matter, said monodentate ligand is selected from the group consisting of halo, hydroxy, carbonyl, amine, nitro, sulfhydryl, pyridine, thiolate, histidine, methionine, cysteine, and dimethylsulfoxide.

In an alternate aspect of the inventive subject matter, said bidentate ligand is selected from the group consisting of substituted or unsubstituted pyridines, amines, diamines, thiols, dithiols, imidazoles, pyrazoles, benzimidazoles, 1,4-dienes, 2-(aminomethyl)pyridines, 2-iminopyridines, substituted bipyridines, phenanthrolines, 8-hydroxyquinolines, and 6-mercaptopurines.

In yet another aspect of the inventive subject matter, said compound is selected from the group consisting of:

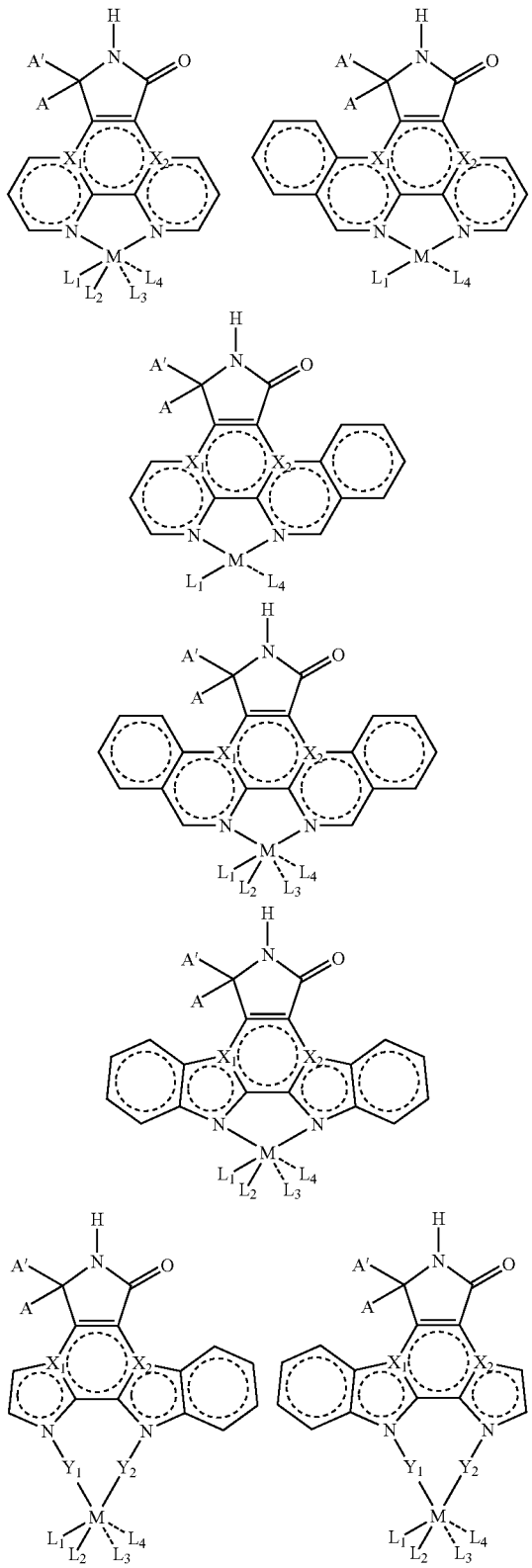

-continued

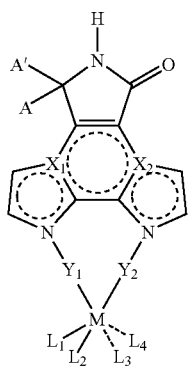 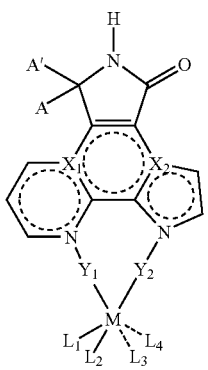 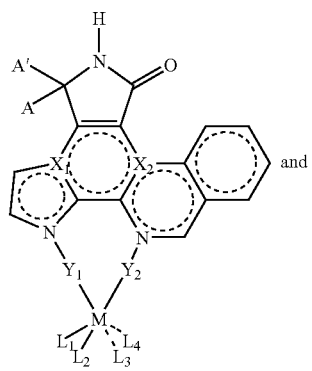

and

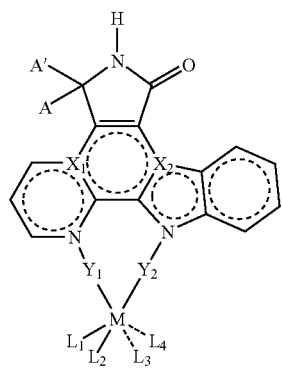 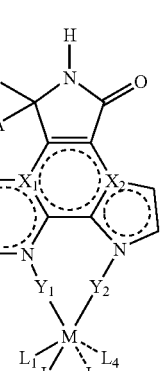 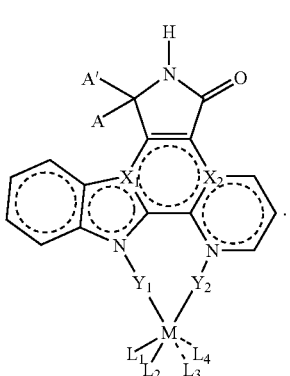

.

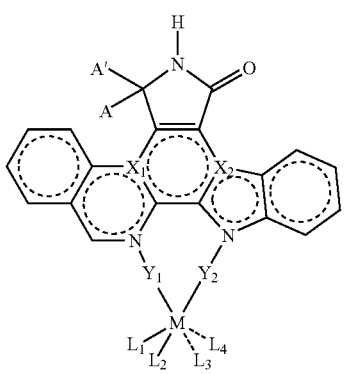

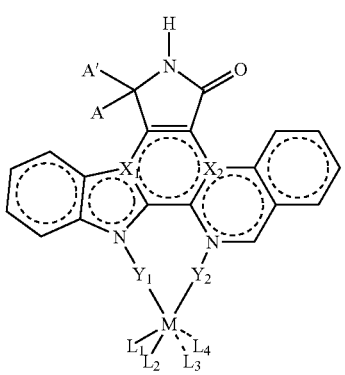 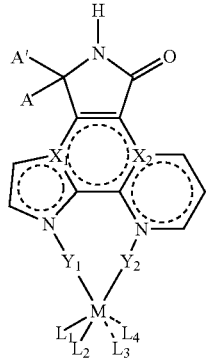

Synthesis of Inventive Compounds

The compounds of the present inventive subject matter may be readily prepared by standard techniques of organic chemistry, utilizing the general synthetic pathways depicted below.

In the preparation of the compounds of the inventive subject matter, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the present inventive subject matter.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

SCHEME I
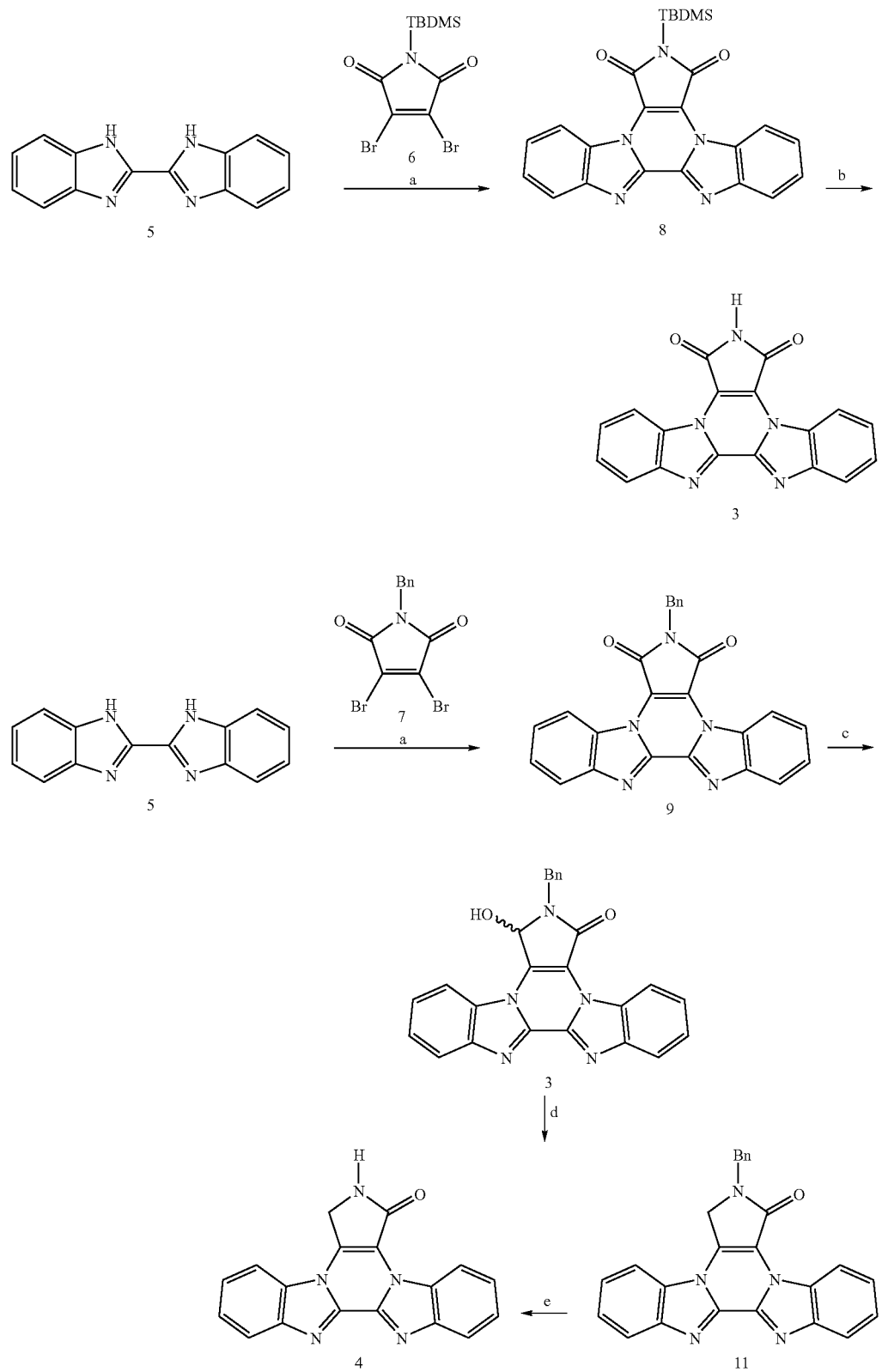
[a]Deprotonation of 5 with 2.1 equiv. of NaH in DMF, followed by addition 6 or 7 (8: 33%, 9: 35%). [b]TBAF, CH$_2$Cl$_2$ (71%). [c]NaBH$_4$, EtOH (90%). [d]First reflux in Ac$_2$O, then addition of Zn and reflux. [e]TFA, H$_2$SO$_4$, anisole, reflux (76%).

As depicted in Scheme I, bisbenzimidazolomaleimide (3) was synthesized in an economical fashion from readily available precursors in two steps by condensing deprotonated bisbenzimidazole (4) with N-TBDMS-2,3-dibromomaleimide (6a) followed by deprotection with TBAF to afford 3.

the two nitrogens and their large distance apart. Interestingly, a comparison with the crystal structure of the free ligand (9) reveals that, upon complexation, the distance between the two coordinating nitrogen atoms decreases from 3.05 Å to 2.80 Å, a remarkable change in length of 8.2%.

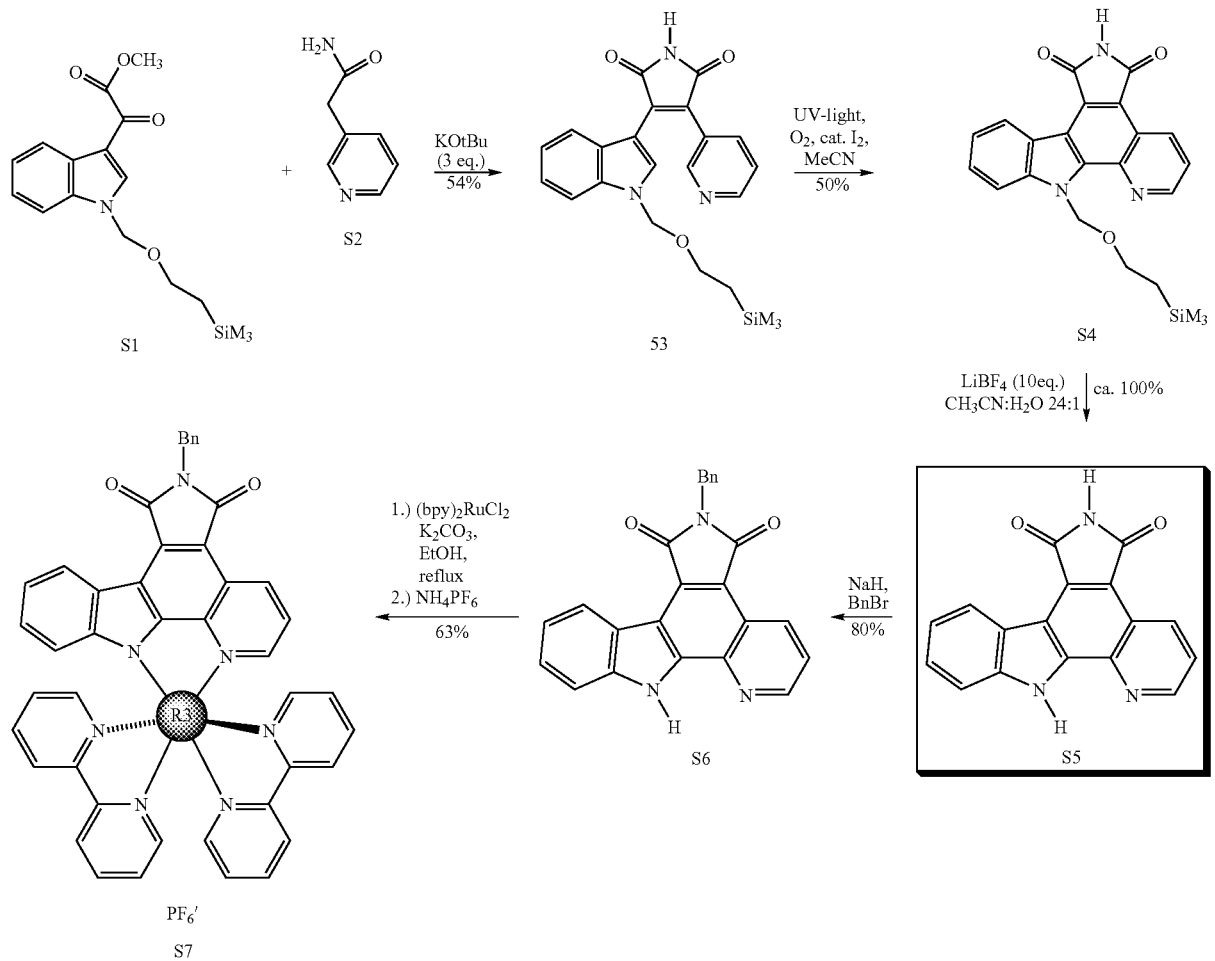

Lactam 4 was obtained by condensing deprotonated bisbenzimidazole 5 with N-benzyl-2,3-dibromomaleimide 7, yielding 9, followed by a reduction and deprotection sequence, as shown in Scheme 1.

Accordingly, one carbonyl group of 9 was first reduced to the alcohol 10 with NaBH$_4$, followed by acetylation of the alcohol with acetic anhydride and reductive elimination to 11 after addition of zinc dust. 9 Finally, deprotection of the benzyl group under acidic conditions yielded the lactam 4.

Despite their unique geometry, having nitrogen donor ligands from two five-membered rings annulated to a central six membered ring, (3) and (4) are able to serve as bidentate ligands. For example, refluxing the benzyl derivative (9) with cis-RuCl$_2$(DMSO) 4 in toluene, yielded diastereoselectively the cis(Cl),cis(DMSO) complex (8b), which isomerized to the cis(Cl),trans(DMSO) isomer upon crystallization from chloroform. The structure reveals that the two benzimidazoles can indeed serve as coordination sites for the ruthenium and that the ligand 9 is, as expected, almost superimposable to the indolocarbazole 2. The ruthenium-nitrogen bonds are remarkably long with 2.15 Å and 2.16 Å, respectively, which we expect are a consequence of both the open biting angle of As depicted by Scheme II, methyl glyoxylate S1 was reacted with acetamide S2, yielding maleimide S3 in 54% yield. Oxidative photocyclization yielded S4 in 50% yield. Only C—C bond formation between the indole-C2 and the pyridine-C2 occurred. The isomeric product which would result from C—C bond formation between the indole-C2 and pyridine-C4 could not be detected. Quantitative SEM-deprotection yielded the plain ligand S5.

Figure 4:
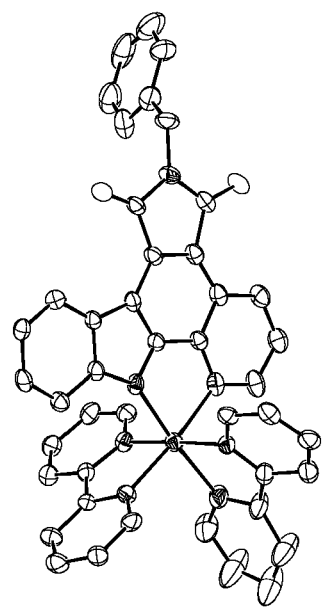
FIG. 4 is a drawing which depicts the X-ray structure of ruthenium complex S7.

In order to demonstrate that S5 can indeed serve as a bidentate ligand, we crystallized ruthenium complex S7, which was obtained as shown in Scheme II. The benzyl group increases the solubility of the ruthenium complex in organic solvents which turned out to be crucial for obtaining well diffracting crystals. The obtained x-ray structure is shown in FIG. 4 and confirms our design: The pyridine ring forms a coordinative bond to the ruthenium center while the indole-N1 undergoes a real s-bond with the ruthenium. We are only aware of one published x-ray structure with a bond between an indole nitrogen and ruthenium.

In addition, it turns out that compound S7 and related compounds are very stable. In fact, no difference can be observed compared to the stability of organic compounds. For example, S7 is completely stable in water, under oxygen, and can withstand the presence of millimolar concentrations of thiols. No signs of decomposition are detected after incubation with a 1 mM solution of 2-mercaptoethanol in methanol overnight.
SCHEME III
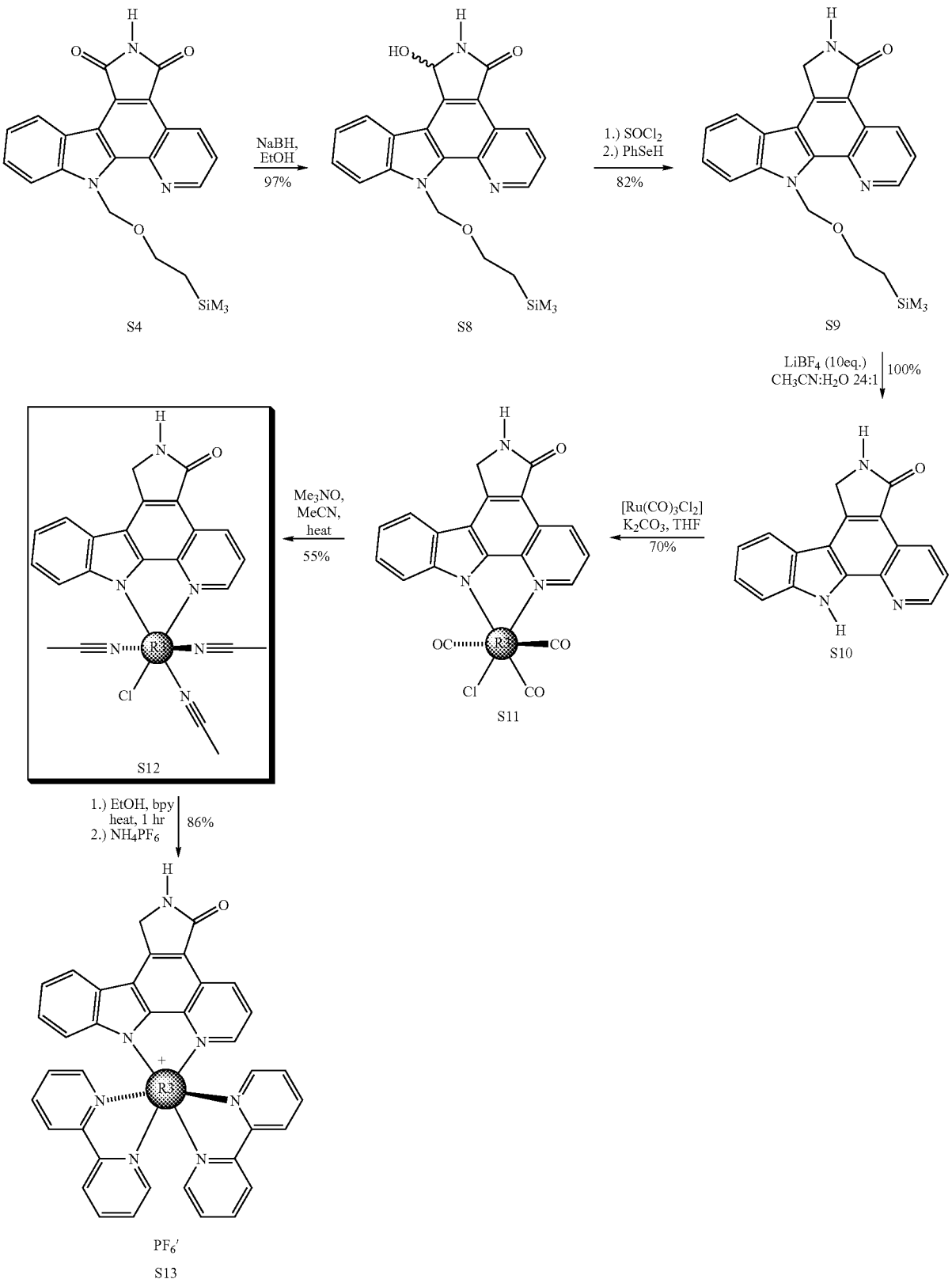

Based on the promising scaffold S5 we developed a route that will allow the synthesis of libraries of ruthenium complexes. Towards this goal, we succeeded in working out a synthetic route to ruthenium complex S12 (equivalent to scaffold 70 in proposal) which, due to its four leaving groups, is an ideal starting point for the synthesis of a diversity of new compounds in a combinatorial fashion. Precursor S12 was synthesized as shown in Scheme III. Maleimide S4 was transformed to the lactam in a two-step reduction procedure yielding S9 in 80% over the two steps. This reduction seems necessary because according to our experiences, the acidity of the maleimide tends to interfere with the coordination chemistry. Compound S9 was subsequently deprotected and transformed into the ruthenium carbonyl compound S11. Following treatment with $Me_3NO$ in acetonitrile under heat generated S12. S12 is remarkably stable despite having four potential leaving groups. For example, S12 can be purified over a conventional silica gel column and can be stored without precaution on the bench. This demonstrates the kinetic inertness of ruthenium compounds. On the other hand, heating S12 in presence of bipyridine to 50-60 EC allows a very efficient introduction of the bidentate ligand. Bipyridine complex S13 was isolated in high yields. S13 is a potent inhibitor for the Abelson protein kinase (Abl) with an $IC_{50}$ of 800 nM in presence of 100:M of ATP. S13 is our currently most potent inhibitor for Abl and an excellent lead structure for the design of more potent and specific inhibitors of Abl by introducing substituents on the bipyridine rings.

Precursor complex S12 has four leaving groups and is thus an ideal starting compound for the synthesis of ruthenium complex-based combinatorial libraries. We are now starting to apply solution phase parallel combinatorial synthesis to the design of libraries with substituted bipyridine and phenanthroline ligands.

Route(s) of Administration

The route(s) of administration of the compounds and compositions of the present inventive subject matter are well known to those skilled in the art (see, for example, "Remington's Pharmaceutical Sciences", 18th Edition, Chapter 86, pp. 1581-1592, Mack Publishing Company, 1990). The compounds and compositions may be administered orally, parenterally, by inhalation spray, topically, rectally, nasally, buccally, vaginally, or via an implanted reservoir in dosage formulations containing conventional non-toxic pharmaceutically-acceptable carriers, adjuvants, and vehicles. The term parenteral as used herein includes subcutaneous, intravenous, intramuscular, intraperitoneally, intrathecally, intraventricularly, intrasternal, and intracranial injection or infusion techniques.

To be effective therapeutically as central nervous system targets, the compounds and compositions should readily penetrate the blood-brain barrier when peripherally administered. Compounds which cannot penetrate the blood-brain barrier can be effectively administered by an intraventricular route.

The compounds and compositions may be administered in the form of sterile injectable preparations, for example, as sterile injectable aqueous or oleaginous suspensions. These suspensions, may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, in a preferred embodiment, the compounds and compositions may be administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule, to further enhance stability and provide release in the intestinal tract to improve absorption, is the best mode of administration currently contemplated.

The compounds may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax, and polyethylene glycols.

Furthermore, the compounds may be administered topically, especially when the conditions addressed for treatment involve areas or organs readily accessible by topical application, including the lower intestinal tract. Suitable topical formulations can be readily prepared for such areas or organs. For example, topical application to the lower intestinal tract can be effected in a rectal suppository formulations (see above) or in suitable enema formulations.

It is envisioned that the continuous administration or sustained delivery of the compounds and compositions of the present inventive subject matter may be advantageous for a given condition. While continuous administration may be accomplished via a mechanical means, such as with an infusion pump, it is contemplated that other modes of continuous or near continuous administration may be practiced. For example, such administration may be by subcutaneous or muscular injections as well as oral pills.

Techniques for formulating a variety of other sustained- or controlled-delivery means, such as liposome carriers, bioerodible particles or beads and depot injections, are also known to those skilled in the art.

Dosage

Dosage levels on the order of about 0.001 mg to about 100 mg per kilogram body weight of the active ingredient compounds or compositions are useful in the treatment of the above conditions, with preferred levels ranging from 200 mg per day to 1600 mg per day. The compounds and compositions of the present inventive subject matter may usually be given in two or three doses daily. Starting with a low dose (200-300 mg) twice daily and slowly working up to higher doses if needed is a preferred strategy. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

EXAMPLES

The following examples are illustrative of the present inventive subject matter and are not intended to be limitations thereon. Unless otherwise indicated, all percentages are based upon 100% by weight of the final composition.

Example 1

Preparation of Inventive Compounds

The following example illustrates the preparation of a preferred active agent provided according to the present inventive subject matter.

General Procedures. NMR spectra were recorded on a spectrometer. Low-resolution mass spectra were obtained using ESI technique. High-resolution mass spectra were obtained using either CI or ES ionization. Infrared spectra were recorded on a FTIR spectrometer. All non-aqueous operations were carried out under dry, oxygen-free, argon atmosphere. Solvents and reagents were used as supplied from the manufacturer.

Compound 8. To a stirred mixture of 1.30 g (5.56 mmol) of 2,2'-bisbenzimidazole in 20 ml dry DMF was added 0.55 g NaH (60% in mineral oil, 13.75 mmol). The resulting mixture was stirred at room temperature for 1 hour, and then 2.05 g (5.5 mmol) of N-TBDMS-2,3-dibromomaleimide was added in one portion under ice bath cooling. The solution was allowed to slowly warm to room temperature and the resulting mixture was stirred for another 12 hours. Thereafter, a 10% solution of $NH_4Cl$ (30 ml) was added to afford a yellow precipitate. The yellow solid was extracted with 300 ml warm chloroform, and the solvent was evaporated to give 0.815 g (33% yield). $^1$H-NMR (DMSO-$d_6$, 500 MHz) d 9.05 (m, 2H), 8.06 (m, 2H), 7.64 (m, 4H), 0.83 (s, 9H), −0.06 (s, 6H). $^{13}$C-NMR (DMSO-$d_6$, 373 K, 125 MHz) d 162.86, 143.51, 139.17, 129.31, 125.4 (br), 124.5 (br), 120.44, 120.01, 119.95, 115.10 (br), 28.29, 25.24, −3.8. HRMS, calcd for $C_{24}H_{23}N_5O_2Si$ (MH$^+$) 442.168034; found 442.169929. IR (KBr, cm$^{-1}$) 2955 (m), 2919 (m), 2861 (m), 1772 (w), 1713 (s), 1655 (w), 1561 (w), 1502 (w), 1449 (s), 1326 (w), 1296 (m), 1091 (w), 1008 (w), 856 (w), 826 (m), 761 (w), 744 (m).

Compound 9. To a stirred mixture of 1.013 g (4.33 mmol) of 2,2'-bisbenzimidazole in 40 ml dry DMF was added 0.36 g NaH (60% in mineral oil, 9 mmol). After 1.5 hours, 1.50 g (4.33 mmol) of N-benzyl-2,3-dibromomaleimide was added in one portion. The resulting mixture was stirred for 24 hours, and then 30 ml of a 10% $NH_4Cl$ solution was added, resulting in a yellow-brown precipitate. The precipitate was filtered, washed with water and ether, dried, and recrystallized from DMSO, yielding 0.635 g (35%). $^1$H-NMR (DMSO-$d_6$, 500 MHz) d 9.04 (m, 2H), 8.07 (m, 2H), 7.65 (m, 4H), 7.47 (d, J=7.2 Hz, 2H), 7.38 (t, J=7.1 Hz, 2H), 7.31 (t, J=7.3 Hz, 1H), 4.96 (s, 2H). $^{13}$C-NMR (DMSO-$d_6$, 373 K, 125 MHz) d 167.81, 149.54, 145.11, 141.56, 135.27, 134.02 (br), 133.10 (br), 131.54 (br), 130.53 (br), 126.13, 126.06, 125.99, 121.0 (br), 47.10. HRMS, calcd for $C_{25}H_{15}N_5O_2$ (MNa$^+$) 440.110183; found 440.112345. IR (KBr, cm$^{-1}$): 3072 (w), 3025 (w), 2931 (w), 1778 (s), 1731 (s), 1666 (m), 1578 (w), 1561 (w), 1502 (w), 1455 (s), 1408 (w), 1373 (m), 1337 (m), 1320 (m), 1267 (w), 1190 (w), 1114 (w), 1049 (w), 1008 (w), 938 (w), 814 (w), 773 (m), 750 (m), 732 (m), 697 (m), 626 (w), 497 (w).

Maleimide 3. To a suspension of compound 8 (0.084 g, 0.19 mmol) in 20 ml $CH_2Cl_2$ was added 0.25 ml (t-Bu)$_4$NF (1.0 M solution in THF), then 0.05 ml acetic acid was added at once. The solvent was removed, the resulting solid washed with MeOH, and air-dried to afford 0.044 g (71%) of 3. The low solubility of 3 combined with its unusual relaxation properties makes it difficult to measure a satisfactory carbon NMR. $^1$H-NMR (DMSO-$d_6$, 500 MHz) d 9.08 (m, 2H), 8.06 (m, 2H), 7.64 (m, 4H). HRMS, calcd for $C_{18}H_9N_5O_3$ (MH$^+$) 328.082613; found 328.083450. IR (KBr, cm$^{-1}$) 3237 (s), 3107 (w), 1772 (m), 1737 (s), 1666 (s), 1520 (w), 1455 (s), 1343 (s), 1296 (s), 1202 (w), 1091 (w), 1008 (w), 973 (w), 914 (w), 820 (w), 761 (m), 744 (s), 720 (m), 662 (w), 644 (w), 485 (s).

Alcohol 10. To a stirred mixture of 0.40 g (0.962 mmol) of 9 in 22 ml EtOH was added 0.04 g $NaBH_4$ (1.06 mmol). Every hour an additional (0.04 g) portion of $NaBH_4$ was added. Over 3 hours, the resulting mixture had turned creamy, and the reaction was complete as observed by TLC analysis. Then 40 ml of water was added to give a pale yellow precipitate. The precipitate was filtered, washed with water and ether, and dried, yielding 0.361 g (90%). $^1$H-NMR (DMSO-$d_6$, 500 MHz) d 9.29 (m, 1H), 8.31 (m, 1H), 8.05-8.03 (m, 2H), 7.68-7.54 (m, 5H), 7.46 (d, J=7.45 Hz, 2H), 7.37 (t, J=7.5 Hz, 2H), 7.29 (t, J=7.4 Hz, 1H), 6.51 (d, J=9.7 Hz, 1H), 5.04 (d, J=15.8 Hz, 1H), 4.58 (d, J=15.9 Hz, 1H). HRMS, calcd for $C_{25}H_{17}N_5O_2Na$ (MNa$^+$) 442.127822; found 440.127995. IR (KBr, cm$^{-1}$) 3225 (br), 2379 (w), 2355 (w), 1713 (s), 1678 (w), 1655 (w), 1637 (w), 1561 (w), 1496 (m), 1461 (s), 1384 (m), 1343 (m), 1331 (m), 1284 (w), 1255 (w), 1220 (w), 1138 (w), 1055 (w), 1008 (w), 761 (m), 744 (s), 703 (m).

Lactam 11. Alcohol 10 (0.361 g, 0.86 mmol) was heated to reflux in 30 ml acetic anhydride for one hour. To the clear yellow solution, activated zinc dust (0.33 g, 5.08 mmol) was added at once and the resulting mixture was heated for another 50 minutes under vigorous stirring. The solution was first evaporated, then 30 ml $NH_4Cl$ were added and extracted with $CH_2Cl_2$ (3, 50 ml). The organic layer was dried over $MgSO_4$ and evaporated under reduced pressure to afford 0.307 g (89%). $^1$H-NMR (DMSO-$d_6$, 500 MHz) d 9.36 (m, 1H), 8.03-7.97 (m, 3H), 7.60-7.52 (m, 4H), 7.45 (d, J=7.3 Hz, 2H), 7.39 (t, J=7.5 Hz, 2H), 7.31 (t, J=7.1 Hz, 1H), 5.25 (s, 2H), 4.88 (s, 2H). HRMS, calcd for $C_{25}H_{17}N_5O$ (MH$^+$) 404.150849; found 404.151135. IR (KBr, cm$^{-1}$): 3448 (m), 1702 (s), 1496 (s), 1478 (s), 1449 (m), 1438 (m), 1390 (m), 1266 (m), 1223 (w), 1036 (w), 1007 (w), 826 (w), 784 (w), 764 (m), 744 (s), 700 (m), 640 (w) and 603 (w).

Lactam 4. A stirred mixture of the product from the previous step 2, (0.190 g, 0.46 mmol), and anisole (0.02 ml, 0.018 mmol) in TFA (20 ml) containing concentrated $H_2SO_4$ (1 ml) was heated to reflux for 40 hours. The resulting dark solution was evaporated under reduced pressure. Ethanol (50 ml) and ether (50 ml) was added to the brown residue, the resulting milky suspension was filtered, washed with ethanol and ether, then dried, affording 0.117 g of 4 (76%). $^1$H-NMR (DMSO-$d_6$, 500 MHz) d 9.35 (m, 1H), 9.17 (s, 1H), 8.05 (m, 2H), 7.98 (m, 1H), 7.60 (m, 2H), 7.53 (m, 2H), 5.19 (s, 2H). HRMS, calcd for $C_{18}H_{11}N_5O$ (MH$^+$) 314.103293; found 314.104185. IR (KBr, cm$^{-1}$): 3234 (m), 1718 (s), 1594 (m), 1571 (w), 1523 (w), 1495 (w), 1436 (w), 1407 (m), 1365 (m), 1342 (m), 1230 (m), 1160 (s), 1077 (w), 1036 (w), 1007 (w), 989 (w), 854 (w), 760 (m), 689 (w), 631 (w) and 584 (w).

Figure 2:
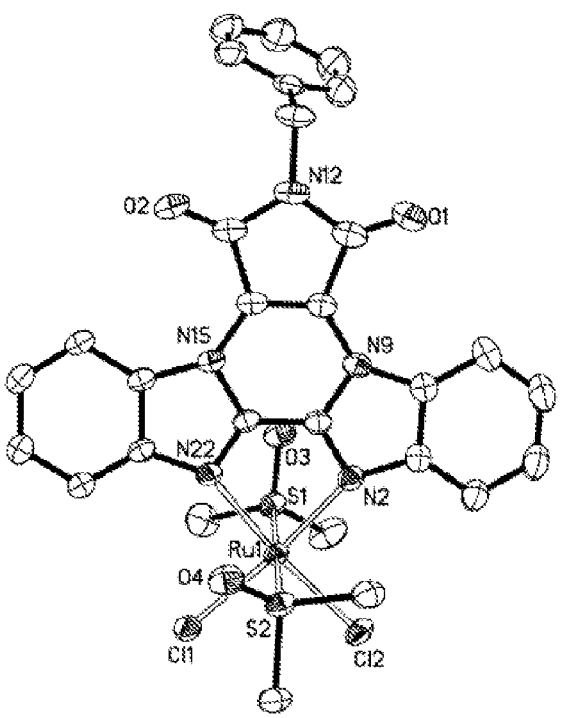
Figure 3:
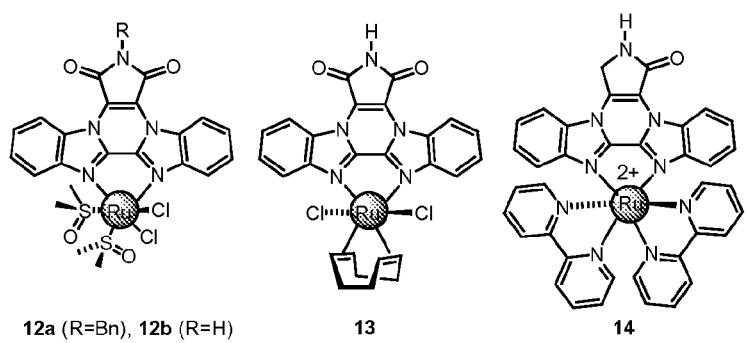
FIG. 3 is a drawing which depicts ruthenium complexes 12-14.

Ruthenium complex 12a. A suspension of 9 (0.0184 g, 0.044 mmol) and cis-RuCl$_2$(DMSO)$_4$ (0.0214 g, 0.044 mmol) in 1 ml toluene was heated under reflux for 12 hrs. Then the mixture was filtered, and the orange solid obtained was washed with toluene and ether, then dried to give 0.029 g (89% yield) of 12a. $^1$H-NMR (DMSO-d$_6$, 500 MHz) d 8.89 (m, 2H), 8.76 (m, 1H), 8.64 (m, 1H), 7.83 (m, 4H), 7.48 (d, J=7.5 Hz, 2H), 7.38 (t, J=7.5 Hz, 2H), 7.31 (t, J=7.2 Hz, 1H), 5.02 (s, 2H), 3.54 (s, 3H), 3.43 (s, 3H), 3.02 (s, 3H), 2.76 (s, 3H). IR (KBr, cm$^{-1}$) 3448 (w), 3020 (w), 2918 (w), 1776 (w), 1713 (s), 1570 (w), 1560 (w), 1493 (m), 1465 (m), 1444 (m), 1400 (s), 1342 (m), 1296 (w), 1221 (w), 1090 (s), 1015 (m), 968 (w), 926 (w), 812 (w), 750 (m), 696 (w), 680 (w), 500 (w). Anal. Calcd for $C_{29}H_{27}Cl_2N_5O_4RuS_2 \times 1.5H_2O$: C, 45.00; H, 3.88; N, 9.05. Found: C, 43.75; H, 3.75; N, 8.46. FIG. 2 depicts the X-ray structure obtained upon crystallization of complex 12a. The complex isomerized to the cis(Cl),trans (DMSO) isomer. ORTEP drawing with 35% probability thermal elipsoids.

Ruthenium complex 12b. A suspension of 8 (0.0209 g, 0.0473 mmol) and cis-RuCl$_2$(DMSO)$_4$ (0.023 g, 0.048 mmol) in toluene (1 ml) was heated under reflux for 12 hrs. The mixture was filtered and the resulting brown solid was washed with toluene, methylene chloride and ether, and dried to give 0.0246 g (79% yield) of 12b. $^1$H-NMR (DMSO-d$_6$, 500 MHz) d 12.3 (s, 1H), 8.86 (m, 2H), 8.72 (m, 1H), 8.61 (m, 1H), 7.79 (m, 4H), 3.51 (s, 3H), 3.41 (s, 3H), 3.00 (s, 3H), 2.74 (s, 3H). IR (KBr, cm$^{-1}$) 3448 (br), 3013 (w), 2919 (w), 1780 (w), 1740 (s), 1448 (s), 1376 (m), 1293 (m), 1093 (s), 1011 (s), 8149 (w), 765 (m), 748 (m), 678 (w) and 492 (m). Anal. Calcd for $C_{22}H_{21}Cl_2N_5O_4RuS_2 \times 0.5H_2O$: C, 39.73; H, 3.31; N, 10.53. Found: C, 40.31; H, 2.97; N, 10.81.

Ruthenium complex 13. A suspension of bis(acetonitrile) dichloro(h$^4$-1,5-cyclooctadiene) ruthenium(II) (0.0196 g, 0.052 mmol) and 8 (0.0206 g, 0.047 mmol) in 1 ml toluene was purged with argon for 20 min and refluxed under argon for 1 hour. Longer reaction times decrease the yield. The reaction mixture was filtered, and the yellow solid obtained was washed with ether and dried to afford 20 mg. $^1$H-NMR (CDCl$_3$-d$_1$, 500 MHz) d 8.97 (m, 1H), 7.66 (m, 4H), 7.58 (m, 2H), 7.17 (m, 1H), 5.28 (s, 4H), 2.77 (br, 4H), 2.18 (d, J=7.8 Hz, 4H), 1.08 (s, 9H), 0.65 (s, 6H). IR (KBr, cm$^{-1}$) 3413 (vs), 2955 (w), 2355 (m), 2320 (m), 2249 (w), 2132 (w), 1737 (m), 1713 (s), 1661 (m), 1643 (m), 1378 (w), 1296 (w), 1220 (w), 1085 (w), 1049 (m), 1026 (s), 997 (s), 826 (m), 761 (m), 738 (w). From this TBDMS-protected ruthenium complex, 14.4 mg (0.0195 mmol) was dissolved in 0.5 ml of DMF, and 0.030 ml tetrabutylammonium fluoride (1.0 M solution in THF) was added. After 2 min, 0.003 ml of glacial acetic acid was added and the solvent was evaporated yielding a brown residue. Methanol was added and the resulting suspension was filtered, giving a brown solid that was washed with methanol and dried to afford 5.2 mg of 13 (26% over both steps). $^1$H-NMR (DMSO-d$_6$, 500 MHz) d 8.94 (d, J=8.4 Hz, 2H), 7.81 (t, J=7.8 Hz, 2H), 7.75 (t, J=7.5 Hz, 2H), 7.59 (d, J=8.3 Hz, 2H), 5.03 (br, 4H), 2.57 (br, 4H), 2.09 (m, 4H). IR (KBr, cm$^{-1}$): 3022 (m), 2963 (m), 1777 (m), 1741 (s), 1682 (m), 1654 (s), 1577 (w), 1547 (w), 1500 (w), 1442 (s), 1377 (s), 1301 (m), 1224 (w), 1089 (w), 1007 (w), 812 (w), 766 (m), 760 (m), 666 (w), and 490 (m). Anal. Calcd for $C_{26}H_{17}Cl_2N_5O_2Ru \times 1.5H_2O$: C, 49.49; H, 3.17; N, 11.1. Found: C, 49.66; H, 3.47; N, 12.06.

Ruthenium complex 14. A mixture of cis-dichlorobis(2,2'-bipyridine)ruthenium(II) dihydrate (0.0336 g, 0.0646 mmol) and AgOSO$_2$CF$_3$ (0.0345 g, 0.1343 mmol) was heated in ethanol (3 ml) to reflux for 1.5 hours. Thereafter, precipitated AgCl was filtered off and 0.02 g of ligand 4 was added. The resulting mixture was refluxed for 40 hours. To the suspension, 5 ml ether was added, and the resulting orange-red solid was washed with ether and dried to give 0.014 g (64% yield) of 14. $^1$H-NMR (DMSO-d$_6$, 500 MHz) d 9.54 (s, 1H), 9.10 (d, J=8.6 Hz, 1H), 8.85 (m, 2H), 8.76 (m, 2H), 8.25 (m, 3H), 8.19-8.08 (m, 6H), 7.69-7.61 (m, 4H), 7.50-7.44 (m, 4H), 6.08 (d, J=8.3 Hz, 1H), 6.01 (d, J=8.4 Hz, 1H), 5.29 (s, 2H). IR (KBr, cm$^{-1}$) 3425 (s), 2367 (m), 2343 (m), 1972 (w), 1725 (w), 1719 (m), 1708 (m), 1684 (w), 1655 (m), 1637 (w), 1602 (w), 1561 (w), 1490 (w), 1467 (m), 1455 (m), 1420 (w), 1219 (s), 1173 (s), 1120 (m), 1032 (s), 1008 (m), 767 (m), 732 (w), 638 (w) and 574 (w). Anal. Calcd for $C_{41}H_{29}F_6N_9O_7RuS_2 \times H_2O$: C, 46.55; H, 2.93; N, 11.92. Found: C, 46.71; H, 3.12; N, 11.32.

Example 2

Protein Kinase Inhibition

We examined the potency of ruthenium complexes 12b, 13, and 14 against a small panel of protein kinases and compared the results to the potency of the free ligands 3 and 4. Table 1 gives the concentrations of compounds required for 50% inhibition (IC$_{50}$). As expected, 3 and 4 have some affinity against most of the tested kinases. The important observation is that upon formation of the ruthenium complexes, affinity and specificity become modulated. For example, the bipyridine complex 14 is the only compound that inhibits protein kinase C (PKC) below 100:M. On the other hand, the COD complex 13 is the best inhibitor for the Abelson tyrosine kinase (Abl) with an IC$_{50}$ of 2:M, which is more than 10 times lower than the IC$_{50}$ of the corresponding free ligand 3. Additionally, the precursor Ru(COD)(CH$_3$CN)$_2$Cl$_2$ does not show any signs of inhibition against Abl even at 100:M. Consequently, the activity of compound 13 requires the entire assembly, kept together by the central ruthenium ion. In order to test if 13 does, as designed, bind to the ATP site, we synthesized a derivative of 13 with the imide hydrogen replaced by a benzyl group. This derivative shows a potency that is strongly reduced by a factor of 25, consistent with the assumption that the imide hydrogen is involved in hydrogen bonding within the adenine binding cleft. Additionally, a Lineweaver-Burk analysis of the initial velocities with Abl at different ATP concentrations and fixed concentrations of ruthenium compound 14 reaffirms ATP competitive binding [see supplementary material for details]. It is also noteworthy that the specificities of COD complex 13 and bipyridine complex 14 are different from that of staurosporine. In our assays, staurosporine is a nanomolar inhibitor for all tested kinases, except for Abl against which it has an IC$_{50}$ of 2:M.

TABLE 1

Inhibition of some protein kinases by ligand 3, 4 and ruthenium complexes 12b, 13, and 14.

| compound | Abl | RSK1 | Src | PKC∀ | ZAP70 |
|---|---|---|---|---|---|
| staurosporine | 2 | <1 | <1 | <1 | <1 |
| 3 | 25 | 30 | >100 | >100 | >100 |
| 4 | 20 | 25 | 60 | >100 | 50 |
| 12b | 10 | 8 | 30 | >100 | 40 |
| 13 | 2 | 8 | 40 | >100 | 30 |
| 14 | 5 | 8 | 30 | 50 | 40 |

$^a$Concentrations required for 50% inhibition (IC$_{50}$) in: M. Determined by phosphorylation of peptide or protein substrates with [8-$^{32}$P]ATP in presence of varying concentrations of inhibitors.

To our knowledge, this is the first report of metal complexes as protein kinase inhibitors. The scaffold 14 is chemically very robust and conformationally rigid, and thus is expected to be a promising lead structure for the development of potent and specific inhibitors of Abl by derivatizing the bipyridine ligands.

Example 3

Kinase Inhibition Assays

Assays for Abl (human, active), RSK1 (rat, active), and ZAP-70 (human, active). Various concentrations of inhibitor were incubated at room temperature in 20 mM MOPS, 30 mM MgCl$_2$, 0.8 mg/ml BSA, 1% DMSO (resulting from the inhibitor stock solution), pH 7.0, in presence of substrate (abltide for Abl: 25 mM, MAPKKAP kinase 2 substrate peptide for RSK1: 50 mM, poly(Glu-Tyr 4:1) for ZAP-70: 0.1 mg/ml) and kinase (Abl: 0.4 ng/ml, RSK1: 0.4 ng/ml, ZAP-70: 5 ng/ml). After 20 min, the reaction was initiated by adding ATP to a final concentration of 100 mM, including 0.04 mCi/ml [g-$^{32}$P]ATP. Reactions were typically performed in a total volume of 25 ml. After 30 min, the reaction was terminated by spotting 20 ml on a 2×2 cm square P81 phosphocellulose paper followed by washing four times with 0.75% phosphoric acid and once with ethanol or acetone. The dried P81 papers were transferred to a scintillation vial and 5 ml of scintillation cocktail were added and the counts per minute (CPM) determined with a Beckmann 6000 scintillation counter. IC$_{50}$ values were defined to be the concentration of inhibitor at which the CPM was 50% of the control sample, corrected by the background.

Assay for c-Src (human, active). Various concentrations of inhibitor were incubated at room temperature in 40 mM Tris-HCl, 32.5 mM MgCl$_2$, 2.5 mM MnCl$_2$, 0.2 mM EGTA, 0.025 mM sodium orthovanadate, 0.2 mM dithiothreitol, 0.8 mg/ml BSA, 1% DMSO (resulting from the inhibitor stock solution), pH 7.5, in presence of c-Src substrate peptide (50 mM) and c-Src kinase (0.125 u/ml). After 20 min, the reaction was initiated by adding ATP to a final concentration of 100 mM, including 0.04 mCi/ml [g-$^{32}$P]ATP. Reactions were typically performed in a total volume of 25 ml. After 30 min the reaction was terminated by spotting 20 ml on a 2×2 cm square P81 phosphocellulose paper followed by washing four times with 0.75% phosphoric acid and once ethanol or acetone. The dried P81 papers were transferred to a scintillation vial and 5 ml of scintillation cocktail were added and the counts per minute (CPM) determined with a Beckmann 6000 scintillation counter. IC$_{50}$ values were defined to be the concentration of inhibitor at which the CPM was 50% of the control sample, corrected by the background.

Assay for PKCa (human, active). Various concentrations of inhibitor were incubated at room temperature in 10 mM HEPES, 0.025% Triton X-100, 10 mM MgCl$_2$, 0.3 mM CaCl$_2$, 0.1 mg/ml phosphatidylserine, 0.01 mg/ml diacylglycerol, 5 mM ∃-glycerophosphate, 0.2 mM sodium orthovanadate, 0.8 mg/ml BSA, 1% DMSO (resulting from the inhibitor stock solution), pH 7.5, in presence of histone H1 (0.05 mg/ml) and PKCa (0.4 ng/ml). After 20 min, the reaction was initiated by adding ATP to a final concentration of 100 mM, including 0.04 mCi/ml [g-$^{32}$P]ATP. Reactions were typically performed in a total volume of 25 ml. After 30 min the reaction was terminated by spotting 20 ml on a 2×2 cm square P81 phosphocellulose paper followed by washing four times with 0.75% phosphoric acid and once ethanol or acetone. The dried P81 papers were transferred to a scintillation vial and 5 ml of scintillation cocktail were added and the counts per minute (CPM) determined with a Beckmann 6000 scintillation counter. IC$_{50}$ values were defined to be the concentration of inhibitor at which the CPM was 50% of the control sample, corrected by the background.

Lineweaver-Burk Analysis. Initial velocities were determined with the antibody beacon tyrosine kinase assay from Molecular Probes. For this, various concentrations of ruthenium complex 14 (0, 0.5 mM, 1.5 mM) were incubated at room temperature in presence of different concentrations of ATP (3 mM to 1000 mM) in 20 mM MOPS (pH 7.0), 30 mM MgCl$_2$, 0.27 mg/ml BSA, 1% DMSO (resulting from the inhibitor stock solution), Abelson kinase (human, active, 0.067 ng/ml), 33.3 nM anti-phosphotyrosine antibody (P-Tyr-100, Molecular Probes), 16.7 nM oregon green ligand (Molecular Probes), and 0.13 mg/ml poly(Glu-Ala-Tyr 6:3: 1). Reactions were carried out in volumes of 75 ml.

Figure 5:
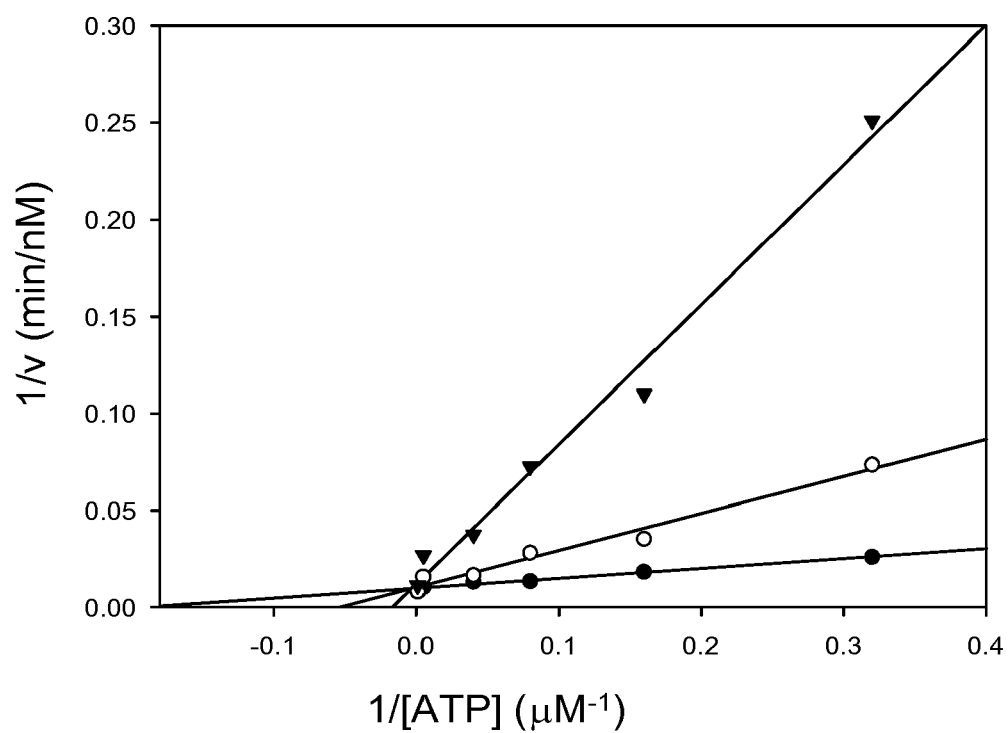
FIG. 5 is a graph which depicts the Lineweaver-Burk analysis of the kinase inhibition assays.

The assay is based on the displacement of the anti-phosphotyrosine antibody-bound oregon green ligand by the formed tyrosine-phosphorylated substrate, resulting in a real-time fluorescence increase. The fluorescence increase was monitored at multiple time points with a fluorescence plate reader (Gemini XS from Molecular Devices) in 96-well plates. Excitation wavelength was 485 nm, emission was measured at 525 nm. Under the used conditions, less than 10% of the substrate was converted to product. Initial velocities were determined by monitoring the fluorescence increase at several time points. A standard curve with a phosphotyrosine-containing peptide (phospho-pp60 c-src from Molecular Probes) allowed to correlate the amount of phosphorylated peptide with the fluorescence increase. All reactions were performed twice. The results are shown in FIG. 5, which depicts double-reciprocal plots of initial velocities against varying ATP concentrations in the presence of 1.5 mM 14 (□), 0.5 mM 14 ("), and no inhibitor (!). The plots intersect at the 1/v axis, confirming that compound 14 binds competitive with respect to ATP.

Example 4

X-Ray Structure Determination $C_{29}H_{27}N_5S_2O_4Cl_2Ru!2$ ¼ CHCl$_3$, crystallizes in the tetragonal space group I4$_1$/a (systematic absences hk0: h=odd, hkl: h+k+l=odd, and 00l: l□4n) with a=31.901 (2) Å, c=15.8767 (9) Å, V=16157 (2) Å$^3$, Z=16 and d$_{calc}$=1.668 g/cm$^3$. X-ray intensity data were collected on a Rigaku Mercury CCD area detector employing graphite-monochromated Mo—K$_a$ radiation (1=0.71069 Å) at a temperature of 143° K. Indexing was performed from a series of four 0.5° oscillation images with exposures of 30 seconds per frame. A hemisphere of data was collected using 90 second exposures and a crystal-to-detector distance of 36 mm. A total of 440 images were collected: one sweep was performed using N-scans from −90° to +90° in 0.5° steps at T=0° and Π=0° with a detector swing angle of −15°; a second sweep was done using T-scans from −20° to +20° in 0.5° steps at Π=−90° and N=0° with a detector swing angle of −15°. Rotation images were processed using CrystalClear,[i] producing a listing of unaveraged F$^2$ and Φ (F$^2$) values which were then passed to the CrystalStructure[ii] program package for further processing and structure solution on a Dell Pentium III computer. A total of 49180 reflections were measured over the ranges 5.1 #22 #54.96°, −41 # h #32, −41 # k #32, −19 # l #19 yielding 9117 unique reflections (R$_{int}$=0.0283). The intensity data were corrected for Lorentz and polarization effects and for absorption. using REQAB[iii] (minimum and maximum transmission 0.811, 1.000).

[i] CrystalClear: Rigaku Corporation, 1999.
[ii] CrystalStructure: Crystal Structure Analysis Package, Rigaku Corp. Rigaku/MSC (2002).
[iii] REQAB4: R. A. Jacobsen, (1994). Private Communication.

The structure was solved by direct methods (SIR97[iv]). The asymmetric unit includes two molecules of chloroform at general positions and one molecule of disordered chloroform on a crystallographic ∉(at ½, ¼, ⅞). Refinement was by full-matrix least squares based on F$^2$ using SHELXL-97.[v] All reflections were used during refinement ($F^2$'s that were experimentally negative were replaced by $F^2$=0). The weighting scheme used was w=1/[$\Phi^2$($F_o^{2)+0.0944P2}$+76.1837P] where P=($F_o^{2+F_2)/3}$. Non-hydrogen atoms were refined anisotropically and hydrogen atoms were refined using a "riding" model. Refinement converged to R1=0.0606 and wR2=0.1594 for 7807 reflections for which F>4$\Phi$(F) and R1=0.0710, wR2=0.1749 and GOF=1.049 for all 9117 unique, non-zero reflections and 478 variables.[vi] The maximum)/$\Phi$ in the final cycle of least squares was 0.002 and the two most prominent peaks in the final difference Fourier were +1.907 and −0.947 e/Å$^3$.

[iv] SIR97: Altomare, A., M. Burla, M. Camalli, G. Cascarano, C. Giacovazzo, A. Guagliardi, A. Moliterni, G. Polidori & R. Spagna (1999). *J. Appl. Cryst.*, 32, 115-119.

[v] SHELXL-97: Program for the Refinement of Crystal Structures, Sheldrick, G. M. (1997), University of Göttingen, Germany.

[vi] $R_1=3\|F_O|-|F_C\|/3|F_O|$ $wR_2=\{3w(F_o2-F_o)^2/3w(F_o^{2)2}\}^{1/2}$ GOF=$\{3w(F_o^{2-}F2)2/(n-p)\}^{1/2}$ where n=the number of reflections and p=the number of parameters refined.

[vii] "ORTEP-II: A Fortran Thermal Ellipsoid Plot Program for Crystal Structure Illustrations". C. K. Johnson (1976) ORNL-5138.

TABLE 2

Summary of Structure Determination of Compound 9

Formula: $C_{125}H_{117}N_{20}S_8O_{16}Cl_{75}Ru_4$
Formula weight: 1014.22
Crystal class: tetragonal
Space group: I4$_1$/a (#88)
Z: 4
Cell constants:

a 31.901(2) Å
c 15.8767(9) Å
V 16157(2) Å$^3$
: 11.13 cm$^{-1}$
crystal size, mm 0.35 × 0.25 × 0.12
$D_{calc}$ 1.668 g/cm$^3$
F(000) 8136
Radiation: Mo-K$_\nabla$(8 = 0.71069 Å)
22 range 5.1-54.96E
hkl collected: −41#h#32; −41#k#32; −19#l#19
No. reflections measured: 49180
No. unique reflections: 9117 ($R_{int}$ = 0.0283)
No. observed reflections 7807 (F > 4$\Phi$)
No. reflections used in refinement 9117
No. parameters 478
R indices (F > 4$\Phi$ $R_1$ = 0.0606
wR$_2$ = 0.1594
R indices (all data) $R_1$ = 0.0710
wR$_2$ = 0.1749
GOF: 1.049
Final Difference Peaks, e/Å$^3$ +1.907, −0.947

TABLE 3

Refined Positional Parameters

| Atom | x | y | z | Ueq, Å$^2$ |
|---|---|---|---|---|
| Ru1 | 0.626579(9) | 0.547749(9) | 0.71208(2) | 0.03333(12) |
| Cl1 | 0.62146(3) | 0.61939(3) | 0.66913(7) | 0.0454(2) |
| Cl2 | 0.66017(3) | 0.56587(3) | 0.84175(7) | 0.0464(2) |
| S1 | 0.56109(3) | 0.54812(3) | 0.77113(7) | 0.0410(2) |
| S2 | 0.69146(3) | 0.54533(3) | 0.65001(7) | 0.0390(2) |
| O1 | 0.57835(12) | 0.32739(10) | 0.6640(2) | 0.0596(9) |
| O2 | 0.52534(10) | 0.39683(10) | 0.4359(2) | 0.0492(7) |
| O3 | 0.53631(10) | 0.50962(11) | 0.7546(2) | 0.0517(7) |
| O4 | 0.69308(10) | 0.53923(11) | 0.5576(2) | 0.0523(8) |
| N1 | 0.62743(10) | 0.48185(10) | 0.7404(2) | 0.0380(7) |
| N2 | 0.59632(10) | 0.52458(10) | 0.5998(2) | 0.0339(6) |
| N3 | 0.59986(10) | 0.42110(10) | 0.6917(2) | 0.0378(7) |
| N4 | 0.56999(9) | 0.46431(10) | 0.5465(2) | 0.0341(6) |
| N5 | 0.54660(12) | 0.35254(12) | 0.5434(2) | 0.0487(9) |
| C1 | 0.60702(12) | 0.46266(12) | 0.6795(2) | 0.0356(8) |

TABLE 3-continued

Refined Positional Parameters

| Atom | x | y | z | Ueq, Å$^2$ |
|---|---|---|---|---|
| C2 | 0.63540(13) | 0.45013(13) | 0.7986(3) | 0.0408(8) |
| C3 | 0.6560(2) | 0.4522(2) | 0.8754(3) | 0.0519(11) |
| H3 | 0.6668 | 0.4773 | 0.8958 | 0.069 |
| C4 | 0.6597(2) | 0.4155(2) | 0.9198(3) | 0.0654(14) |
| H4 | 0.6732 | 0.4159 | 0.9717 | 0.087 |
| C5 | 0.6439(2) | 0.3774(2) | 0.8899(3) | 0.0666(14) |
| H5 | 0.6477 | 0.3533 | 0.9219 | 0.089 |
| C6 | 0.6229(2) | 0.3746(2) | 0.8144(3) | 0.0575(12) |
| H6 | 0.6119 | 0.3493 | 0.7949 | 0.076 |
| C7 | 0.61887(13) | 0.41169(13) | 0.7690(3) | 0.0409(8) |
| C8 | 0.57875(12) | 0.40117(12) | 0.6272(3) | 0.0384(8) |
| C9 | 0.56884(14) | 0.35586(14) | 0.6179(3) | 0.0477(10) |
| C10 | 0.54260(12) | 0.39108(13) | 0.5012(3) | 0.0425(9) |
| C11 | 0.56418(11) | 0.42169(12) | 0.5585(3) | 0.0370(8) |
| C12 | 0.55912(10) | 0.49613(12) | 0.4898(2) | 0.0330(7) |
| C13 | 0.53702(12) | 0.49616(14) | 0.4138(2) | 0.0400(8) |
| H13 | 0.5260 | 0.4717 | 0.3911 | 0.053 |
| C14 | 0.53244(14) | 0.5339(2) | 0.3747(3) | 0.0475(10) |
| H14 | 0.5180 | 0.5351 | 0.3238 | 0.063 |
| C15 | 0.54879(13) | 0.5715(2) | 0.4087(3) | 0.0451(9) |
| H15 | 0.5448 | 0.5965 | 0.3798 | 0.060 |
| C16 | 0.57044(12) | 0.57177(13) | 0.4838(3) | 0.0401(8) |
| H16 | 0.5810 | 0.5965 | 0.5062 | 0.053 |
| C17 | 0.57584(11) | 0.53354(12) | 0.5247(2) | 0.0340(7) |
| C18 | 0.59195(11) | 0.48437(12) | 0.6092(2) | 0.0339(7) |
| C19 | 0.5289(2) | 0.31322(14) | 0.5113(3) | 0.0556(12) |
| H19a | 0.5454 | 0.2898 | 0.5319 | 0.067 |
| H19b | 0.5303 | 0.3131 | 0.4502 | 0.067 |
| C20 | 0.4840(2) | 0.30786(12) | 0.5385(3) | 0.0478(10) |
| C21 | 0.4751(2) | 0.2986(2) | 0.6217(4) | 0.0634(13) |
| H21 | 0.4969 | 0.2953 | 0.6601 | 0.084 |
| C22 | 0.4340(2) | 0.2941(2) | 0.6482(4) | 0.079(2) |
| H22 | 0.4282 | 0.2875 | 0.7041 | 0.105 |
| C23 | 0.4019(2) | 0.2994(2) | 0.5918(4) | 0.079(2) |
| H23 | 0.3742 | 0.2966 | 0.6094 | 0.105 |
| C24 | 0.4107(2) | 0.3088(2) | 0.5091(4) | 0.072(2) |
| H24 | 0.3889 | 0.3121 | 0.4707 | 0.095 |
| C25 | 0.4511(2) | 0.3133(2) | 0.4831(3) | 0.0599(13) |
| H25 | 0.4565 | 0.3202 | 0.4273 | 0.080 |
| C26 | 0.5602(2) | 0.5560(2) | 0.8816(3) | 0.072(2) |
| H26a | 0.5316 | 0.5566 | 0.9008 | 0.107 |
| H26b | 0.5735 | 0.5821 | 0.8949 | 0.107 |
| H26c | 0.5748 | 0.5335 | 0.9089 | 0.107 |
| C27 | 0.5293(2) | 0.5906(2) | 0.7372(5) | 0.070(2) |
| H27a | 0.5291 | 0.5917 | 0.6768 | 0.106 |
| H27b | 0.5404 | 0.6164 | 0.7591 | 0.106 |
| H27c | 0.5012 | 0.5867 | 0.7574 | 0.106 |
| C28 | 0.72298(14) | 0.50541(14) | 0.6965(3) | 0.0502(10) |
| H28a | 0.7114 | 0.4784 | 0.6834 | 0.075 |
| H28b | 0.7236 | 0.5092 | 0.7564 | 0.075 |
| H28c | 0.7510 | 0.5072 | 0.6745 | 0.075 |
| C29 | 0.72297(14) | 0.59033(14) | 0.6727(3) | 0.0490(10) |
| H29a | 0.7494 | 0.5879 | 0.6443 | 0.074 |
| H29b | 0.7276 | 0.5921 | 0.7323 | 0.074 |
| H29c | 0.7088 | 0.6151 | 0.6537 | 0.074 |
| C30 | 0.7069(4) | 0.6083(3) | 0.4260(5) | 0.115(4) |
| H30 | 0.7087 | 0.5859 | 0.4681 | 0.152 |
| Cl3 | 0.74127(8) | 0.59571(13) | 0.3429(2) | 0.1405(14) |
| Cl4 | 0.7203(2) | 0.65494(12) | 0.4749(2) | 0.197(2) |
| Cl5 | 0.65641(9) | 0.60945(14) | 0.3885(2) | 0.160(2) |
| C31 | 0.5134(2) | 0.4366(2) | 0.8729(4) | 0.0615(14) |
| H31 | 0.5280 | 0.4569 | 0.8371 | 0.082 |
| Cl6 | 0.54519(7) | 0.42798(10) | 0.96041(14) | 0.1122(9) |
| Cl7 | 0.46588(6) | 0.45928(8) | 0.90134(12) | 0.0929(7) |
| Cl8 | 0.50535(7) | 0.39138(7) | 0.8111(2) | 0.1013(7) |
| C32 | 0.5000 | 0.2500 | 0.8750 | 0.25(3) |
| Cl9 | 0.5394(2) | 0.2798(2) | 0.8291(4) | 0.140(2) |

Ueq = $1/3[U_{11}(aa^*)^2 + U_{22}(bb^*)^2 + U_{33}(cc^*)^2 + 2U_{12}aa^*bb^*\cos g + 2U_{13}aa^*cc^*\cos b + 2U_{23}bb^*cc^*\cos a]$

TABLE 4

Refined Thermal Parameters (U's)

| Atom | $U_{11}$ | $U_{22}$ | $U_{33}$ | $U_{23}$ | $U_{13}$ | $U_{12}$ |
|---|---|---|---|---|---|---|
| Ru1 | 0.0350(2) | 0.0328(2) | 0.0323(2) | −0.00874(11) | −0.00519(11) | 0.00050(11) |
| Cl1 | 0.0523(6) | 0.0349(5) | 0.0490(6) | −0.0082(4) | −0.0105(4) | 0.0014(4) |
| Cl2 | 0.0477(5) | 0.0506(6) | 0.0408(5) | −0.0148(4) | −0.0133(4) | 0.0028(4) |
| S1 | 0.0374(5) | 0.0467(5) | 0.0391(5) | −0.0093(4) | −0.0010(4) | 0.0012(4) |
| S2 | 0.0369(5) | 0.0372(5) | 0.0429(5) | −0.0113(4) | −0.0028(4) | −0.0020(4) |
| O1 | 0.074(2) | 0.038(2) | 0.067(2) | −0.003(2) | 0.008(2) | −0.003(2) |
| O2 | 0.044(2) | 0.056(2) | 0.047(2) | −0.0192(14) | −0.0008(13) | −0.0103(13) |
| O3 | 0.040(2) | 0.059(2) | 0.056(2) | −0.008(2) | 0.0022(13) | −0.0089(13) |
| O4 | 0.055(2) | 0.055(2) | 0.047(2) | −0.0163(14) | 0.0052(14) | −0.0043(14) |
| N1 | 0.038(2) | 0.037(2) | 0.039(2) | −0.0063(13) | −0.0042(13) | 0.0025(13) |
| N2 | 0.035(2) | 0.033(2) | 0.034(2) | −0.0064(12) | −0.0014(12) | −0.0008(12) |
| N3 | 0.040(2) | 0.032(2) | 0.042(2) | −0.0055(13) | 0.0077(13) | −0.0002(13) |
| N4 | 0.0299(14) | 0.038(2) | 0.034(2) | −0.0073(12) | 0.0029(12) | −0.0051(12) |
| N5 | 0.052(2) | 0.042(2) | 0.052(2) | −0.016(2) | 0.013(2) | −0.015(2) |
| C1 | 0.035(2) | 0.034(2) | 0.038(2) | −0.0060(14) | 0.0029(14) | 0.0002(14) |
| C2 | 0.042(2) | 0.042(2) | 0.038(2) | −0.002(2) | 0.002(2) | 0.005(2) |
| C3 | 0.058(3) | 0.054(3) | 0.044(2) | −0.003(2) | −0.009(2) | 0.010(2) |
| C4 | 0.077(4) | 0.072(3) | 0.047(3) | 0.008(2) | −0.013(2) | 0.012(3) |
| C5 | 0.089(4) | 0.057(3) | 0.053(3) | 0.015(2) | −0.002(3) | 0.015(3) |
| C6 | 0.066(3) | 0.049(3) | 0.058(3) | 0.009(2) | 0.006(2) | 0.008(2) |
| C7 | 0.040(2) | 0.044(2) | 0.038(2) | −0.002(2) | 0.007(2) | 0.006(2) |
| C8 | 0.035(2) | 0.036(2) | 0.044(2) | −0.008(2) | 0.009(2) | −0.0021(14) |
| C9 | 0.051(2) | 0.040(2) | 0.053(3) | −0.011(2) | 0.017(2) | −0.007(2) |
| C10 | 0.034(2) | 0.045(2) | 0.048(2) | −0.018(2) | 0.015(2) | −0.010(2) |
| C11 | 0.030(2) | 0.039(2) | 0.042(2) | −0.012(2) | 0.010(2) | −0.0069(14) |
| C12 | 0.025(2) | 0.040(2) | 0.034(2) | −0.0080(14) | 0.0041(13) | −0.0032(13) |
| C13 | 0.033(2) | 0.052(2) | 0.035(2) | −0.011(2) | 0.001(2) | −0.008(2) |
| C14 | 0.042(2) | 0.066(3) | 0.035(2) | −0.006(2) | −0.005(2) | −0.003(2) |
| C15 | 0.042(2) | 0.052(2) | 0.041(2) | 0.000(2) | −0.003(2) | 0.003(2) |
| C16 | 0.037(2) | 0.044(2) | 0.039(2) | −0.005(2) | −0.001(2) | −0.001(2) |
| C17 | 0.028(2) | 0.041(2) | 0.033(2) | −0.0098(14) | 0.0029(13) | −0.0008(14) |
| C18 | 0.034(2) | 0.037(2) | 0.032(2) | −0.0105(14) | 0.0015(14) | −0.0018(14) |
| C19 | 0.063(3) | 0.037(2) | 0.067(3) | −0.022(2) | 0.013(2) | −0.010(2) |
| C20 | 0.057(3) | 0.029(2) | 0.057(3) | −0.006(2) | 0.002(2) | −0.014(2) |
| C21 | 0.061(3) | 0.067(3) | 0.062(3) | 0.013(2) | −0.007(2) | −0.013(2) |
| C22 | 0.080(4) | 0.094(5) | 0.062(4) | 0.021(3) | 0.000(3) | −0.028(3) |
| C23 | 0.063(3) | 0.088(4) | 0.086(4) | 0.015(3) | −0.004(3) | −0.028(3) |
| C24 | 0.060(3) | 0.080(4) | 0.075(4) | 0.008(3) | −0.016(3) | −0.029(3) |
| C25 | 0.073(3) | 0.053(3) | 0.053(3) | −0.001(2) | −0.005(2) | −0.025(2) |
| C26 | 0.058(3) | 0.115(5) | 0.041(3) | −0.026(3) | 0.009(2) | −0.017(3) |
| C27 | 0.048(3) | 0.057(3) | 0.106(5) | 0.004(3) | 0.004(3) | 0.016(2) |
| C28 | 0.043(2) | 0.038(2) | 0.069(3) | −0.011(2) | −0.006(2) | 0.004(2) |
| C29 | 0.044(2) | 0.045(2) | 0.058(3) | −0.008(2) | −0.006(2) | −0.009(2) |
| C30 | 0.187(10) | 0.102(6) | 0.055(4) | 0.011(4) | −0.017(5) | −0.076(6) |
| Cl3 | 0.0734(14) | 0.220(4) | 0.128(2) | −0.014(2) | −0.0137(13) | 0.033(2) |
| Cl4 | 0.332(6) | 0.162(3) | 0.097(2) | −0.008(2) | 0.007(3) | −0.162(4) |
| Cl5 | 0.087(2) | 0.259(4) | 0.133(2) | −0.080(3) | 0.045(2) | −0.017(2) |
| C31 | 0.057(3) | 0.076(4) | 0.051(3) | 0.012(3) | 0.006(2) | 0.002(3) |
| Cl6 | 0.0828(13) | 0.175(3) | 0.0792(13) | 0.0230(13) | −0.0087(10) | 0.0335(14) |
| Cl7 | 0.0681(10) | 0.133(2) | 0.0777(12) | 0.0064(11) | 0.0073(8) | 0.0281(10) |
| Cl8 | 0.0958(14) | 0.0771(12) | 0.131(2) | −0.0100(12) | 0.0128(12) | −0.0136(10) |
| C32 | 0.33(4) | 0.33(4) | 0.09(2) | 0.000 | 0.000 | 0.000 |
| Cl9 | 0.142(4) | 0.119(4) | 0.158(5) | −0.001(3) | 0.004(3) | −0.001(3) |

The form of the anisotropic displacement parameter is: $\exp[-2p^2(a^{*2}U_{11}h^2 + b^{*2}U_{22}k^2 + c^{*2}U_{33}l^2 + 2b^*c^*U_{23}kl + 2a^*c^*U_{13}hl + 2a^*b^*U_{12}hk)]$.

TABLE 5

Bond Distances (Å)

| Ru1-N1 | 2.150(3) | Ru1-N2 | 2.158(3) | Ru1-S1 | 2.2898(11) |
|---|---|---|---|---|---|
| Ru1-S2 | 2.2936(10) | Ru1-Cl1 | 2.3907(11) | Ru1-Cl2 | 2.3918(10) |
| S1-O3 | 1.484(3) | S1-C26 | 1.772(5) | S1-C27 | 1.777(5) |
| S2-O4 | 1.481(3) | S2-C28 | 1.782(5) | S2-C29 | 1.789(4) |
| O1-C9 | 1.206(6) | O2-C10 | 1.188(6) | N1-C1 | 1.316(5) |
| N1-C2 | 1.394(5) | N2-C18 | 1.299(5) | N2-C17 | 1.389(5) |
| N3-C1 | 1.359(5) | N3-C8 | 1.381(5) | N3-C7 | 1.402(5) |
| N4-C18 | 1.375(5) | N4-C11 | 1.386(5) | N4-C12 | 1.400(5) |

TABLE 5-continued

Bond Distances (Å)

| | | | | | |
|---|---|---|---|---|---|
| N5-C9 | 1.383(6) | N5-C10 | 1.406(6) | N5-C19 | 1.467(5) |
| C1-C18 | 1.399(6) | C2-C3 | 1.387(6) | C2-C7 | 1.415(6) |
| C3-C4 | 1.374(7) | C4-C5 | 1.397(9) | C5-C6 | 1.377(8) |
| C6-C7 | 1.392(6) | C8-C11 | 1.354(6) | C8-C9 | 1.487(6) |
| C10-C11 | 1.501(5) | C12-C13 | 1.397(5) | C12-C17 | 1.420(5) |
| C13-C14 | 1.364(7) | C14-C15 | 1.413(6) | C15-C16 | 1.378(6) |
| C16-C17 | 1.393(6) | C19-C20 | 1.505(7) | C20-C25 | 1.382(7) |
| C20-C21 | 1.384(7) | C21-C22 | 1.385(9) | C22-C23 | 1.371(9) |
| C23-C24 | 1.377(9) | C24-C25 | 1.359(8) | C30-Cl5 | 1.718(11) |
| C30-Cl4 | 1.730(8) | C30-Cl3 | 1.762(11) | C31-Cl7 | 1.740(6) |
| C31-Cl6 | 1.742(6) | C31-Cl8 | 1.762(7) | C32-Cl9#1 | 1.735(5) |
| C32-Cl9 | 1.735(5) | C32-Cl9#2 | 1.735(5) | C32-Cl9#3 | 1.735(5) |

TABLE 6

Bond Angles (Δ)

| | | | | | |
|---|---|---|---|---|---|
| N1-Ru1-N2 | 80.98(12) | N1-Ru1-S1 | 86.05(9) | N2-Ru1-S1 | 86.09(9) |
| N1-Ru1-S2 | 92.60(9) | N2-Ru1-S2 | 92.14(9) | S1-Ru1-S2 | 177.92(4) |
| N1-Ru1-Cl1 | 174.44(9) | N2-Ru1-Cl1 | 93.51(9) | S1-Ru1-Cl1 | 92.84(4) |
| S2-Ru1-Cl1 | 88.35(4) | N1-Ru1-Cl2 | 92.91(9) | N2-Ru1-Cl2 | 173.89(9) |
| S1-Ru1-Cl2 | 93.16(4) | S2-Ru1-Cl2 | 88.49(4) | Cl1-Ru1-Cl2 | 92.59(4) |
| O3-S1-C26 | 106.5(3) | O3-S1-C27 | 105.9(2) | C26-S1-C27 | 100.5(3) |
| O3-S1-Ru1 | 114.17(13) | C26-S1-Ru1 | 114.9(2) | C27-S1-Ru1 | 113.6(2) |
| O4-S2-C28 | 107.2(2) | O4-S2-C29 | 106.6(2) | C28-S2-C29 | 100.0(2) |
| O4-S2-Ru1 | 117.49(14) | C28-S2-Ru1 | 110.8(2) | C29-S2-Ru1 | 113.2(2) |
| C1-N1-C2 | 103.8(3) | C1-N1-Ru1 | 107.2(3) | C2-N1-Ru1 | 148.3(3) |
| C18-N2-C17 | 104.5(3) | C18-N2-Ru1 | 107.0(2) | C17-N2-Ru1 | 148.1(3) |
| C1-N3-C8 | 115.2(4) | C1-N3-C7 | 105.1(3) | C8-N3-C7 | 139.6(4) |
| C18-N4-C11 | 115.1(3) | C18-N4-C12 | 104.7(3) | C11-N4-C12 | 140.1(3) |
| C9-N5-C10 | 112.8(3) | C9-N5-C19 | 124.1(4) | C10-N5-C19 | 123.2(4) |
| N1-C1-N3 | 115.6(4) | N1-C1-C18 | 121.7(3) | N3-C1-C18 | 122.6(3) |
| C3-C2-N1 | 129.3(4) | C3-C2-C7 | 120.7(4) | N1-C2-C7 | 110.0(4) |
| C4-C3-C2 | 116.8(5) | C3-C4-C5 | 122.4(5) | C6-C5-C4 | 122.0(5) |
| C5-C6-C7 | 116.0(5) | C6-C7-N3 | 132.4(4) | C6-C7-C2 | 122.2(4) |
| N3-C7-C2 | 105.4(3) | C11-C8-N3 | 122.8(4) | C11-C8-C9 | 108.5(4) |
| N3-C8-C9 | 128.7(4) | O1-C9-N5 | 126.2(4) | O1-C9-C8 | 128.2(5) |
| N5-C9-C8 | 105.6(4) | O2-C10-N5 | 126.3(4) | O2-C10-C11 | 129.9(4) |
| N5-C10-C11 | 103.8(4) | C8-C11-N4 | 122.7(3) | C8-C11-C10 | 109.3(4) |
| N4-C11-C10 | 128.0(4) | C13-C12-N4 | 132.9(3) | C13-C12-C17 | 121.7(4) |
| N4-C12-C17 | 105.4(3) | C14-C13-C12 | 116.6(4) | C13-C14-C15 | 122.3(4) |
| C16-C15-C14 | 121.5(4) | C15-C16-C17 | 117.4(4) | N2-C17-C16 | 129.7(3) |
| N2-C17-C12 | 109.8(3) | C16-C17-C12 | 120.5(4) | N2-C18-N4 | 115.5(3) |
| N2-C18-C1 | 122.9(3) | N4-C18-C1 | 121.5(3) | N5-C19-C20 | 111.3(4) |
| C25-C20-C21 | 118.6(5) | C25-C20-C19 | 121.8(5) | C21-C20-C19 | 119.6(5) |
| C20-C21-C22 | 120.4(5) | C23-C22-C21 | 119.8(6) | C22-C23-C24 | 119.8(6) |
| C25-C24-C23 | 120.4(6) | C24-C25-C20 | 121.0(5) | Cl5-C30-Cl4 | 111.6(7) |
| Cl5-C30-Cl3 | 109.2(4) | Cl4-C30-Cl3 | 112.3(5) | Cl7-C31-Cl6 | 111.4(3) |
| Cl7-C31-Cl8 | 111.0(3) | Cl6-C31-Cl8 | 113.6(4) | Cl9#1-C32-Cl9 | 100.1(2) |
| Cl9#1-C32-Cl9#2 | 100.1(2) | Cl9-C32-Cl9#2 | 130.4(4) | Cl9#1-C32-Cl9#3 | 130.4(4) |
| Cl9-C32-Cl9#3 | 100.1(2) | Cl9#2-C32-Cl9#3 | 100.1(2) | | |

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

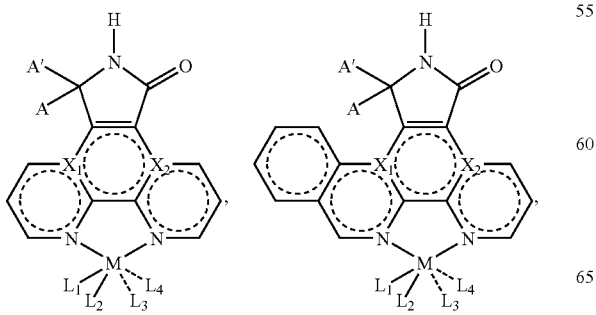

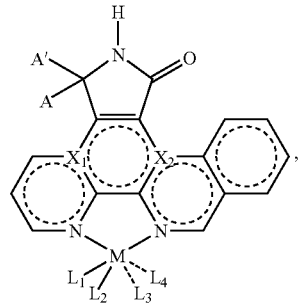

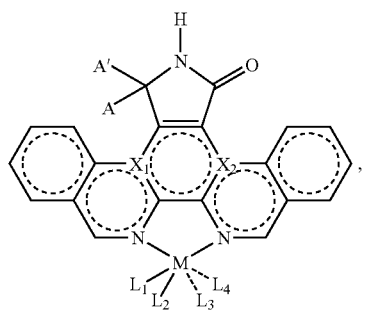

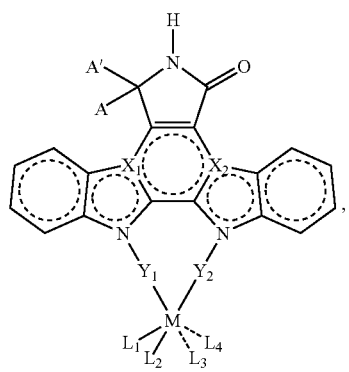

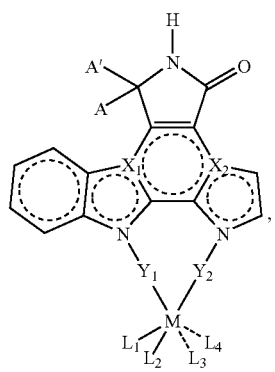

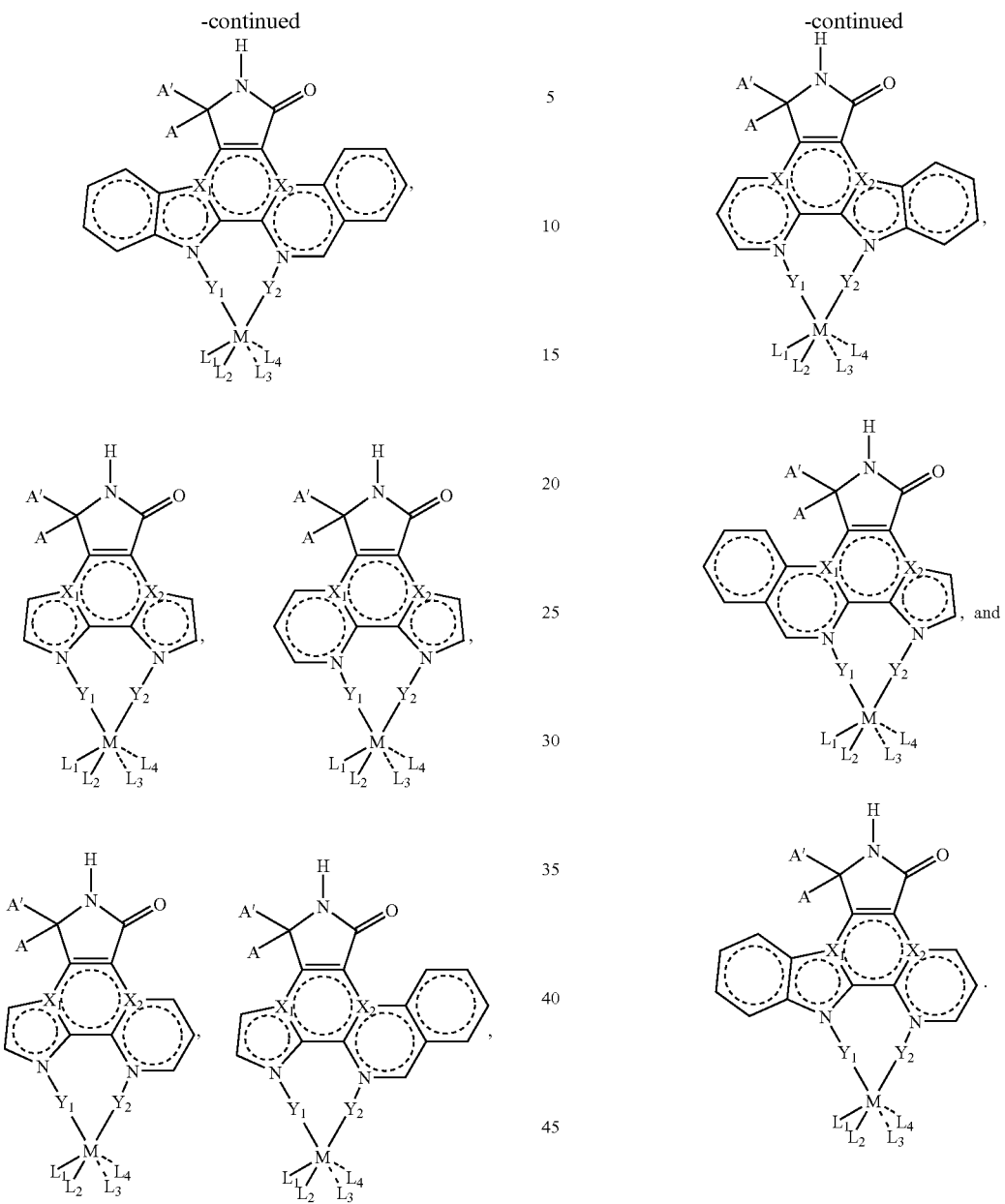

We claim:

1. A method for inhibiting Src-c, Abl, ZAP-70, or RSK1 protein kinase activity in a subject having cancer comprising administering to said subject a therapeutically effective amount of a compound of formula I:

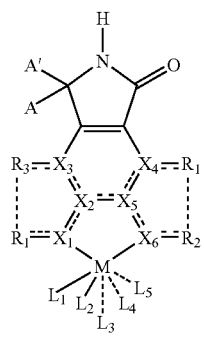

I or a pharmaceutically acceptable salt or ester thereof, wherein:

$X_1, X_2, X_3, X_4, X_5$, and $X_6$ are each independently N, C, S, O, B, or Si;

$R_1, R_2, R_3$, and $R_4$ are each independently:

1,2-methylenedioxy, alkenoxy, alkoxy, alkylamino, alkylaryloxy, alkylthio, amido, amino, aminoalkyl, arylalkyloxy, aryloxy, azo, benzyl, benzyloxy, $C_1$-$C_9$ alkoxy, $C_2$-$C_9$ alkenyloxy, $C_3$-$C_8$ cycloalkyl, $C_5$-$C_7$ cycloalkenyl, carbonyl, carboxy, carboxylic and heterocyclic moieties cyano, diazo, ester, formanilido, halo, haloalkyl, hydrogen, hydroxyl, hydroxymethyl, imino, isocyano, isonitrilo, nitrilo, nitro, nitroso, O-benzyl, O-phenyl, phenoxy, phenyl, sulfhydryl, sulfonyl, sulfonylsulfoxy, thio, thioalkyl, thiocarbonyl, thiocyano, thioester, thioformamido, trifluoromethoxy, trifluoromethyl, straight or branched chain $C_1$-$C_9$ alkyl, straight or branched chain $C_1$-$C_9$ alkyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O—($C_1$-$C_9$ straight or branched alkyl), straight or branched chain $C_2$-$C_9$ alkenyl or alkynyl, and straight or branched chain $C_2$-$C_9$ alkenyl or alkynyl substituted with one or more halo, trifluoromethyl, nitro, $C_1$-$C_6$ straight or branched chain alkyl, $C_2$-$C_6$ straight or branched chain alkenyl, hydroxy, $C_1$-$C_4$ alkoxy, $C_2$-$C_4$ alkenyloxy, phenoxy, benzyloxy, amino, or Ar, O—($C_2$-$C_9$ straight or branched chain alkenyl), or Ar, and/or $R_1$ and $R_2$ are taken together to form a mono-, bi- or tricyclic, carbo- or heterocyclic ring, wherein the ring is either unsubstituted or substituted, wherein the individual ring size for a monocyclic ring is 5-7 members and for a bicyclic or tricyclic ring is 3-8 members, and wherein a heterocyclic ring contains 1-5 heteroatom(s) selected from the group consisting of O, N, and S, and/or $R_3$ and $R_4$ are taken together to form a mono-, bi- or tricyclic, carbo- or heterocyclic ring, wherein the ring is either unsubstituted or substituted, wherein the individual ring size for a monocyclic ring is 5-7 members and for a bicyclic or tricyclic ring is 3-8 members, and wherein a heterocyclic ring contains 1-5 heteroatom(s) comprising O, N, or S;

Ar is a mono-, bi-, or tricyclic, carbo- or heterocyclic ring, wherein the ring is either unsubstituted or substituted in one or more position(s) with halo, hydroxyl, nitro, trifluoromethyl, $C_1$-$C_6$ straight or branched chain alkyl or alkenyl, $C_1$-$C_4$ alkoxy, $C_1$-$C_4$ alkenyloxy, phenoxy, benzyloxy, or amino; wherein the individual ring size for a moncyclic ring is 5-7 members and for a bicyclic or tricyclic ring is 3-8 members; and wherein the heterocyclic ring contains 1-5 heteroatom(s) comprising O, N, or S;

M is Ru, Pt, Tc, Re, Os, Rh, Ir, Pd, Au, Cu, Fe, Co, or Cr;

A and A' are each independently hydrogen, hydroxy, hydroxymethyl, $C_1$-$C_6$ straight or branched chain alkyl, $C_2$-$C_6$ straight or branched chain alkenyl, O—($C_1$-$C_6$ straight or branched chain alkyl), or O—($C_2$-$C_6$ straight or branched chain alkenyl); or, A and A' are taken together as =O; and each $L_1$-$L_n$ is independently a monodentate ligand capable of acting as a ligand for said metal M, and/or $L_1$ and $L_2$ are taken together as a bidentate ligand capable of acting as a ligand for said metal M, and/or $L_1, L_2$, and $L_3$ are taken together as a tridentate ligand capable of acting as a ligand for said metal M, and/or $L_1, L_2, L_3$ and $L_4$ are taken together as a tetradentate ligand capable of acting as a ligand for said metal M; and n is 2, 3, 4, or 5;

at least one pair of $R^1$ and $R^2$ taken together and $R^3$ and $R^4$ taken together forming a mono-, bi- or tricyclic, carbo-, or heterocyclic ring.

2. The method of claim 1, wherein each said $L_1$-$L_n$, individually as a monodentate ligand or taken together as a bidentate ligand, a tridentate ligand, or a tetradentate ligand, is halo, hydroxy, carbonyl, amine, nitro, sulfhydryl, pyridine, thiolate, histidine, methionine, cysteine, dimethylsulfoxide, substituted or unsubstituted pyridines, substituted or unsubstituted amines, substituted or unsubstituted diamines, substituted or unsubstituted thiols, substituted or unsubstituted dithiols, substituted or unsubstituted imidazoles, substituted or unsubstituted pyrazoles, substituted or unsubstituted benzimidazoles, substituted or unsubstituted 1,4-dienes, substituted or unsubstituted 2-(aminomethyl)pyridines, substituted or unsubstituted 2-iminopyridines, substituted bipyridines, substituted or unsubstituted phenanthrolines, substituted or unsubstituted 8-hydroxyquinolines, substituted or unsubstituted 6-mercaptopurines, or substituted or unsubstituted phosphines.

3. The method of claim 1, wherein said $X_1, X_2, X_3, X_4, X_5$, and $X_6$ are each independently N or C.

4. The method of claim 1, wherein said M is Ru or Pt.

5. The method of claim 1, wherein said $R_1$ and $R_2$ are taken together for form a monocyclic 5- or 6-membered ring, or a bicyclic indene, indene derivative, naphthalene, or naphthalene derivative ring, and wherein said ring is carbocyclic or heterocyclic.

6. The method of claim 1, wherein said $R_3$ and $R_4$ are taken together to form a monocyclic 5 or 6 membered ring, or a bicyclic indene, indene derivative, naphthalene, or naphthalene derivative ring, and wherein said ring is carbocyclic or heterocyclic.

7. The method of claim 1, wherein said compound is of formula II

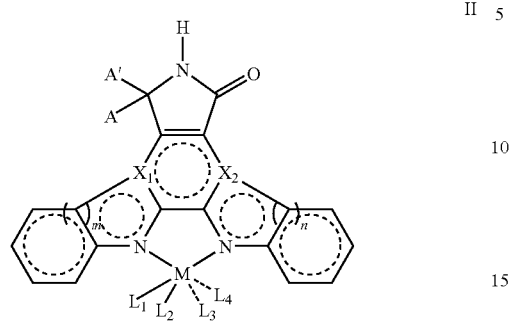

II or a pharmaceutically acceptable salt or ester thereof, wherein:
A is H,
A' is H, or
A and A' taken together are =O;
$X_1$ is N or C;
$X_2$ is N or C;
m is 1 or 2;
n is 1 or 2;
M is Ru or Pt; and
each $L_1$, $L_2$, $L_3$, and $L_4$ is independently a monodentate ligand capable of acting as a ligand for said metal M, and/or
$L_1$ and $L_2$ are taken together as a bidentate ligand capable of acting as a ligand for said metal M, and/or
$L_3$ and $L_4$ are taken together as a bidentate ligand capable of acting as a ligand for said metal M.

8. The method of claim 7, wherein at least one of $X_1$ and $X_2$ is N.
9. The method of claim 7, wherein $X_1$ and $X_2$ are each N.
10. The method of claim 7, wherein m is 1 and n is 1.
11. The method of claim 7, wherein at least one of $L_1$, $L_2$, $L_3$, and $L_4$ is a monodentate ligand comprising halo, hydroxy, carbonyl, amine, nitro, sulfhydryl, pyridine, thiolate, histidine, methionine, cysteine, or dimethylsulfoxide.
12. The method of claim 7, wherein at least one of $L_1$ and $L_2$ or $L_3$, and $L_4$ are a bidentate ligand comprising substituted or unsubstituted pyridines, amines, diamines, thiols, dithiols, imidazoles, pyrazoles, benzimidazoles, 1,4-dienes, 2-(aminomethyl)pyridines, 2-iminopyridines, substituted bipyridines, phenanthrolines, 8-hydroxyquinolines, or 6-mercaptopurines.
13. The method of claim 7, wherein said compound is one or more of: